(12) United States Patent
Tsutsui et al.

(10) Patent No.: US 7,498,068 B2
(45) Date of Patent: Mar. 3, 2009

(54) LIQUID-CRYSTAL ALIGNING AGENT, LIQUID-CRYSTAL ALIGNMENT FILM COMPRISING THE SAME, AND LIQUID-CRYSTAL ELEMENT

(75) Inventors: Kimiaki Tsutsui, Funabashi (JP); Kohei Goto, Funabashi (JP); Hirobumi Shida, Funabashi (JP); Masahide Ishizuya, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 11/587,089

(22) PCT Filed: Apr. 27, 2005

(86) PCT No.: PCT/JP2005/008055

§ 371 (c)(1),
(2), (4) Date: Oct. 20, 2006

(87) PCT Pub. No.: WO2005/105892

PCT Pub. Date: Nov. 10, 2005

(65) Prior Publication Data

US 2007/0224370 A1  Sep. 27, 2007

(30) Foreign Application Priority Data

Apr. 28, 2004 (JP) .............................. 2004-132611
Mar. 11, 2005 (JP) .............................. 2005-068290

(51) Int. Cl.
  *C09K 19/56* (2006.01)

(52) U.S. Cl. ..................... 428/1.26; 428/1.25; 349/123
(58) Field of Classification Search ....... 428/1.25–1.26, 428/473.5, 474.4; 349/135, 123; 257/643
See application file for complete search history.

(56) References Cited

U.S. PATENT DOCUMENTS

| 3,899,309 | A | * | 8/1975 | Hoehn et al. ................ 95/54 |
| 4,670,325 | A | * | 6/1987 | Bakos et al. ............... 428/209 |
| 5,229,484 | A | * | 7/1993 | Wolf et al. ................ 528/322 |
| 5,571,579 | A | * | 11/1996 | Kato et al. ................ 428/1.25 |

FOREIGN PATENT DOCUMENTS

| JP | 5 72539 | | 3/1993 |
| JP | 06-016629 | * | 1/1994 |
| JP | 6 82794 | | 3/1994 |
| JP | 8 248424 | | 9/1996 |
| JP | 10 7906 | | 1/1998 |
| JP | 2001 72770 | | 3/2001 |
| JP | 2002 20487 | | 1/2002 |
| JP | 2002 322275 | | 11/2002 |
| JP | 2003 344859 | | 12/2003 |
| WO | 03 005114 | | 1/2003 |

* cited by examiner

*Primary Examiner*—Keith D Hendricks
*Assistant Examiner*—Sophie Hon
(74) *Attorney, Agent, or Firm*—Oblon, Spivak, McClelland, Maier & Neustadt, P.C.

(57) ABSTRACT

A liquid crystal aligning agent capable of forming a liquid crystal alignment film having favorable electrical characteristics, and excellent in the storage stability and the productivity.

8 Claims, 1 Drawing Sheet

LIQUID-CRYSTAL ALIGNING AGENT, LIQUID-CRYSTAL ALIGNMENT FILM COMPRISING THE SAME, AND LIQUID-CRYSTAL ELEMENT

TECHNICAL FIELD

The present invention relates to a liquid crystal aligning agent to be used for formation of a liquid crystal display device, and a liquid crystal alignment film and a liquid crystal display device employing it.

BACKGROUND ART

Liquid crystal display devices utilized for monitors of cellphones and personal computers, televisions, etc., are display devices having such a structure that liquid crystal molecules are sandwiched between liquid crystal alignment films each formed on a substrate, and utilizing a response of the liquid crystal molecules aligned in a certain direction by the liquid crystal alignment films to the voltage.

The liquid crystal alignment film is formed from a liquid crystal aligning agent, and determines the alignment of liquid crystal molecules and the pretilt angle of liquid crystal molecules and has substantial influences over electrical characteristics of the display devices, and thereby has a major role in the liquid crystal display device.

Heretofore, liquid crystal alignment films to improve characteristics of display devices have been developed. For example, it has been proposed to provide a liquid crystal alignment film capable of providing a display device having a high voltage holding ratio and a low residual charge by use of varnish containing a polyamic acid obtainable by condensing a diamine containing bis(aminomethyl)-bicyclo[2,2,1]heptane as the main component and a tetracarboxylic dianhydride, a partially imidated polyamic acid and a polyimide (for example, Patent Document 1). Further, a liquid crystal alignment film having improved alignment of liquid crystal by using a specific aliphatic diamine and an aromatic tetracarboxylic dianhydride has been proposed (for example, Patent Document 2).

However, in a case where an alicyclic or aliphatic diamine is used, it may form a salt with the corresponding amic acid, and if the salt has a low solubility, the reaction may terminate in some cases. Further, even if the salt has a high solubility, it is required to continue stirring until the formed salt disappears, and the reaction will take a long time as compared with a usual case. Accordingly, a process for producing a polyamic acid ester employing a silylamide type sililation reagent and a polyimide obtainable from the polyamic acid ester has been proposed (for example, Patent Document 3).

On the other hand, an aromatic diamine has good polymerization reactivity, but depending upon the type of the acid dianhydride to be reacted, the obtained polyamic acid may be non-uniformalized or may undergo gelation during storage at low temperature in some cases.

Since the productivity and the stability of the polyamic acids have substantial influences over the productivity and the stability of a liquid crystal aligning agent in some cases, the liquid crystal aligning agent has been desired to be capable of improving characteristics (particularly electrical characteristics) of the liquid crystal alignment film, in addition to be easily produced and have favorable storage stability.

Patent Document 1: JP-A-10-7906
Patent Document 2: JP-A-8-248424
Patent Document 3: JP-A-2002-322275

DISCLOSURE OF THE INVENTION

Object to be Accomplished by the Invention

The present invention has been made in view of the above circumstances, and it is an object of the present invention to provide a liquid crystal aligning agent capable of forming a liquid crystal alignment film having favorable electrical characteristics, and excellent in the storage stability and the productivity.

Means to Accomplish the Object

The present inventors have conducted extensive studies to achieve the above object and as a result, have found that the following liquid crystal aligning agent having excellent characteristics can be obtained by using a diamine compound which has not been employed, as a diamine component to be polymerized with a tetracarboxylic dianhydride component to form a polyamic acid or to form a polyimide obtainable by cyclodehydration of the polyamic acid, and accomplished the present invention. Some of the diamine compounds to be used in the present invention are novel also as diamine compounds.

Namely, the present invention provides the following.

1. A liquid crystal aligning agent comprising at least one member selected from a polyamic acid obtained by polymerization of a diamine component with a tetracarboxylic dianhydride component, and a polyimide obtained by cyclodehydration of the polyamic acid, characterized in that the diamine component contains at least one of diamines represented by the following formula [1]:

$$H_2N\text{-}A\text{-}R\text{—}NH_2 \qquad [1]$$

wherein A is a bivalent organic group comprising a benzene ring or an aromatic condensed ring, provided that one or more optional hydrogen atoms in the benzene ring or the aromatic condensed ring may be substituted by a monovalent organic group other than an amino group, and R is a $C_{1\text{-}10}$ bivalent saturated hydrocarbon group.

2. The liquid crystal aligning agent according to the above 1, wherein A in the formula [1] is a bivalent aromatic group selected from the formulae [2-1] to [2-4]:

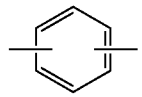

[2-1]

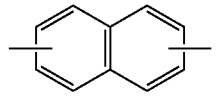

[2-2]

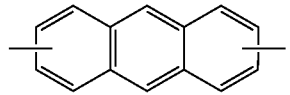

[2-3]

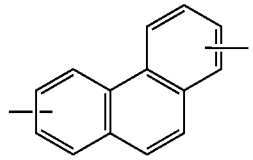

[2-4]

provided that one or more hydrogen atoms in the benzene ring or the aromatic condensed ring may be substituted by a monovalent organic group other than an amino group.

3. The liquid crystal aligning agent according to the above 1 or 2, wherein R in the formula [1] is represented by the following formula [3]:

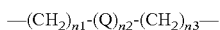  [3]

wherein Q is a $C_{3-7}$ hydrocarbon ring, each of n1 and n3 is an integer of from 0 to 7, and n2 is an integer of 0 or 1, provided that n1, n2 and n3 are not simultaneously 0.

4. The liquid crystal aligning agent according to the above 3, wherein R is —$(CH_2)_{n1}$—, —$(CH_2)_{n1}$-$(Q)_{n2}$ or -$(Q)_{n2}$-$(CH_2)_{n3}$—.

5. The liquid crystal aligning agent according to the above 3 or 4, wherein Q is cyclobutane, cyclopentane or cyclohexane.

6. The liquid crystal aligning agent according to the above 1, wherein the diamine component contains a diamine represented by the formula [4].

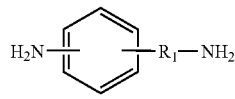  [4]

wherein $R_1$ is a $C_{1-10}$ bivalent saturated hydrocarbon group, provided that one or more optional hydrogen atoms in the benzene ring may be substituted by a monovalent organic group other than an amino group.

7. The liquid crystal aligning agent according to the above 1, wherein the diamine component contains at least one of diamines represented by the formula [5]:

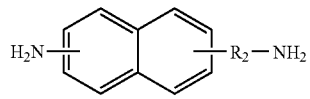  [5]

wherein $R_2$ is a $C_{1-10}$ bivalent saturated hydrocarbon group, provided that one or more optional hydrogen atoms in the naphthalene ring may be substituted by a monovalent organic group other than an amino group.

8. The liquid crystal aligning agent according to any one of the above 1 to 7, wherein the reaction ratio of the tetracarboxylic dianhydride component: the diamine component is from 1:0.8 to 1:1.2 by molar ratio.

9. A liquid crystal alignment film obtained by employing the liquid crystal aligning agent as defined in any one of the above 1 to 8.

10. A liquid crystal display device employing the liquid crystal alignment film as defined in the above 9.

11. 6-Aminonaphthalenemethylamine.

12. 2-(6-Animonaphthalene)ethylamine.

EFFECTS OF THE INVENTION

According to the liquid crystal aligning agent of the present invention, a liquid crystal alignment film excellent in electrical characteristics can be obtained, and a liquid crystal display device can be suitably used. Further, the liquid crystal aligning agent per se is excellent in the stability and the storage stability.

BEST MODE FOR CARRYING OUT THE INVENTION

Figure 1:
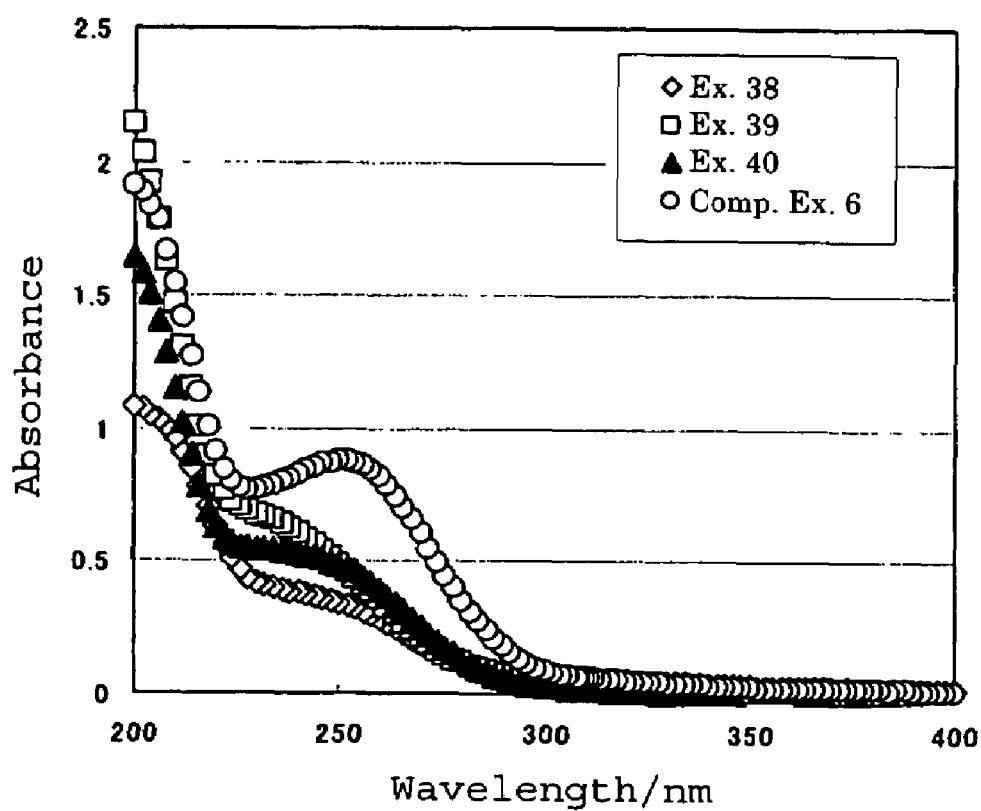
FIG. 1 illustrates UV absorption spectra in Examples 38 to 40 and Comparative Example 6.

Now, the present invention will be described in detail.

The present invention provides a liquid crystal aligning agent comprising at least one member selected from a polyamic acid obtained by polymerizing a diamine component and a tetracarboxylic dianhydride component as monomer components constituting the polymer, and a polyimide obtained by cyclodehydration of the polyamic acid, characterized in that the diamine component contains at least one of diamines represented by the following formula [1]:

  [1]

wherein A is a bivalent organic group comprising a benzene ring or an aromatic condensed ring, provided that one or more optional hydrogen atoms in the benzene ring or the aromatic condensed ring may be substituted by a monovalent organic group other than an amino group, and R is a $C_{1-10}$ bivalent saturated hydrocarbon group.

The diamine represented by the formula [1] to be used in the present invention has such a structure that one amino group is directly bonded to the aromatic ring in A and the other amino group is bonded to the $C_{1-10}$ saturated hydrocarbon group. And, A in the formula [1] is a bivalent organic group selected from a benzene ring and an organic ring represented by a ring having a plurality of benzene rings condensed (hereinafter referred to as an aromatic condensed ring).

Specific examples of A are mentioned below, but A is not limited thereto.

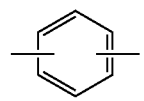  [2-1]

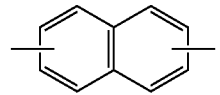  [2-2]

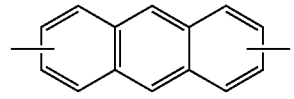  [2-3]

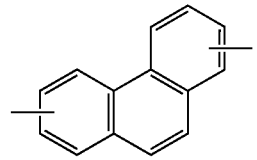  [2-4]

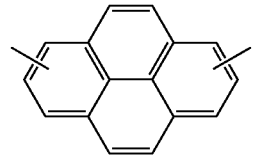  [2-5]

-continued

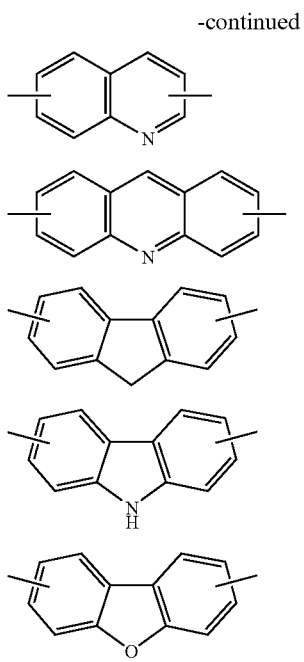

[2-6]

[2-7]

[2-8]

[2-9]

[2-10]

(in the formulae, one or more optional hydrogen atoms in the aromatic ring or the condensed ring may be substituted by a monovalent organic group other than an amino group).

In the present invention, A in the formula [1] is present in the structure of the polyamic acid or the polyimide, and is a portion considered to have an effect of improving the alignment of liquid crystal and the charge accumulation characteristics of the liquid crystal alignment film. Although the reason is not clear, when A is a π-conjugated system aromatic group, more favorable charge accumulation characteristics of the liquid crystal alignment film will be achieved, such being favorable. Further, when the number of the benzene rings or the condensed rings in A is small or when the condensed ring in A is a condensed ring having two or three benzene rings condensed, the storage stability of the liquid crystal aligning agent can be kept favorable, such being favorable.

In the present invention, particularly, A in the formula [1] is preferably a bivalent organic group represented by the above formula [2-1] or [2-2]. A is particularly preferably the formula [2-1], whereby effects will be achieved such that the absorbance of the liquid crystal alignment film in the visible to UV region will be lower and that a polyamic acid or a polyimide having a high solubility will easily be obtained. For example, when A is the formula [2-1], by combination with a diamine component for a polyamic acid which will become insoluble by the imidation reaction, a polyimide is obtained in some cases. Further, A is particularly preferably the formula [2-2], whereby more favorable charge accumulation characteristics will be achieved.

Now, R in the formula [1] will be described. In general, if a polyamic acid or polyimide skeleton is rigid, i.e. if the glass transition temperature is high, the storage stability of the liquid crystal aligning agent is poor in some cases. In order to overcome such a problem, it is desirable to impart plasticity to the polyamic acid or polyimide skeleton. Considering the voltage holding characteristics and the alignment of liquid crystal of the liquid crystal alignment film, R is a $C_{1-10}$ bivalent saturated hydrocarbon group. R is a linear, branched or cyclic saturated hydrocarbon group, and is preferably a bivalent organic group containing no aromatic ring. Since R does not contain an aromatic group, such an effect will also be achieved that the absorbance of the liquid crystal alignment film in the visible to ultraviolet (UV) region will be low. R is preferably a $C_{1-6}$ saturated hydrocarbon group from the viewpoint of the charge accumulation characteristics. Further, it is preferably a linear saturated hydrocarbon from the viewpoint of the alignment of liquid crystal.

Preferred R in the present invention is represented by the following formula [3]:

$$-(CH_2)_{n1}-(Q)_{n2}-(CH_2)_{n3}- \qquad [3]$$

In the formula [3], Q is a $C_{3-7}$ hydrocarbon ring, preferably a cyclobutane ring, a cyclopentane ring or a cyclohexane ring, particularly preferably a cyclohexane ring having a stable cyclic structure. Each of n1 and n3 is an integer of from 0 to 7, preferably from 0 to 3. n2 is an integer of 0 or 1. Here, n1, n2 and n3 are not simultaneously 0.

Specific examples of a preferred diamine represented by the formula [1] are mentioned below, but the diamine is not limited thereto.

For example, in a case where A in the formula [1] is any one of the formulae [2-1] to [2-4], as the diamine wherein R has a cyclic structure, diamines represented by the formulae [6] to [9] may be mentioned:

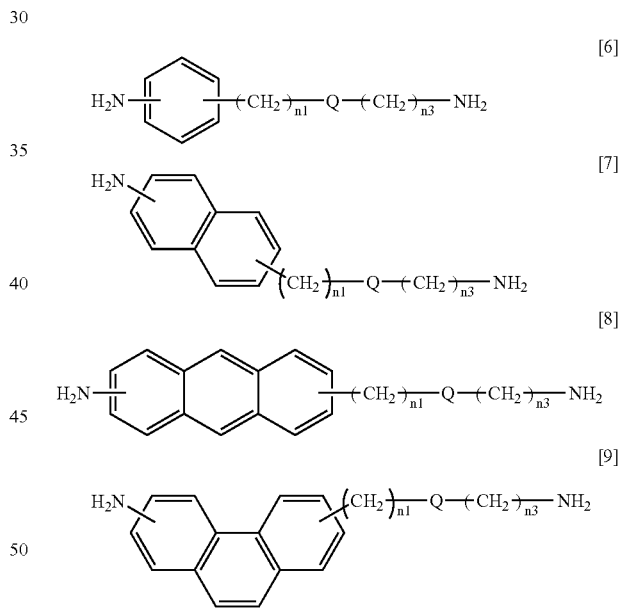

[6]

[7]

[8]

[9]

In the above formulae [6] to [9], Q, n1 and n3 are as defined above, and the total of the number of carbon atoms in Q and the hydrocarbon ring, n1 and n3 is preferably an integer of at most 10. In the formulae, one or more optional hydrogen atoms in the aromatic ring or the hydrocarbon ring may be substituted by a monovalent organic group other than an amino group. Further, as specific examples in the case of condensed rings of the formulae [2-5] to [2-10], similar compounds in accordance with the cases of the formulae [2-1] to [2-4] may be mentioned.

Further, as specific examples in the case of the formula [6], e.g. diamines of the formulae [10] to [16] may be mentioned:

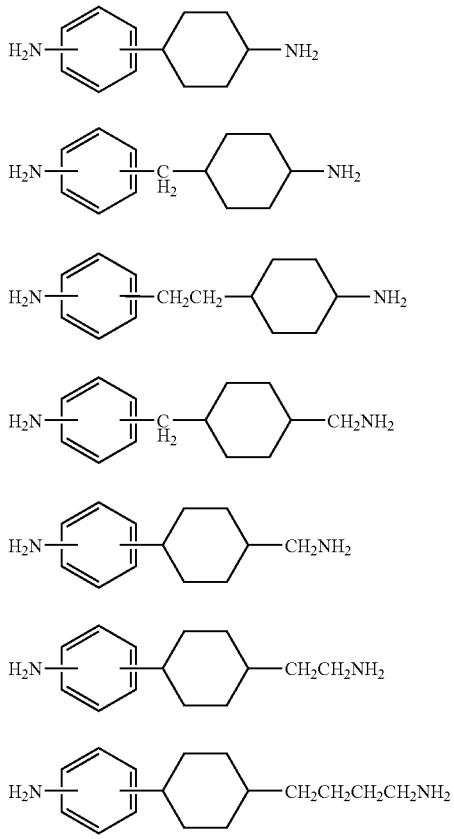

In the diamines of the formulae [10] to [16], one or more optional hydrogen atoms in the benzene ring may be substituted by a monovalent organic group other than an amino group. Further, an optional hydrogen atom in the cyclic structure in R may be substituted by a monovalent alkyl group. Further, as specific examples in the case of condensed rings of the formulae [7] to [9], similar compounds in accordance with the case of the formula [6] may be mentioned.

As a diamine wherein R is a saturated hydrocarbon group having a branched structure, as specific examples in a case where A in the formula [1] is the formula [2-1], e.g. diamines of the formulae [17] to [26] may be mentioned:

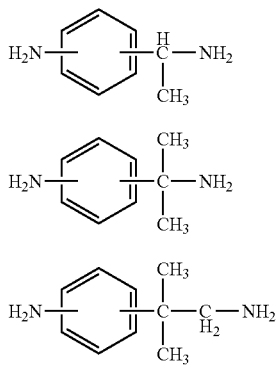

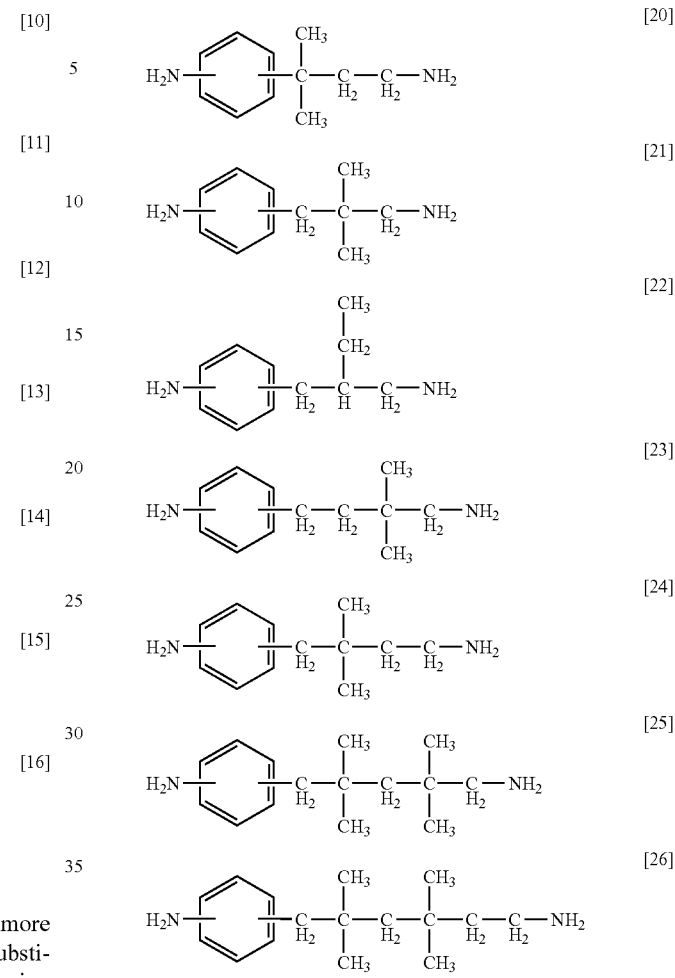

In the diamines of the formulae [17] to [26], one or more optional hydrogen atoms in the benzene ring may be substituted by a monovalent organic group other than an amino group. Further, as specific examples in a case where A in the formula [1] is any one of condensed rings of the formulae [2-2] to [2-10], similar compounds in accordance with the formula [2-1] may be mentioned.

As a diamine wherein R is a linear saturated hydrocarbon group, for example, in a case where A in the formula [1] is the formula [2-1] or is a ring comprising 2 to 3 benzene rings condensed such as the formulae [2-2] to [2-4], diamines represented by the formulae [27] to [31] may be mentioned:

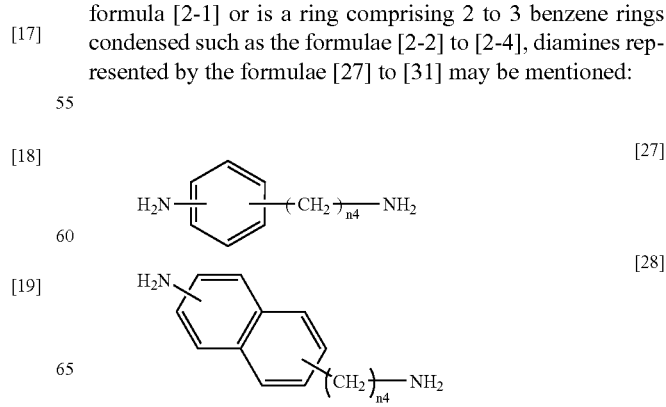

-continued
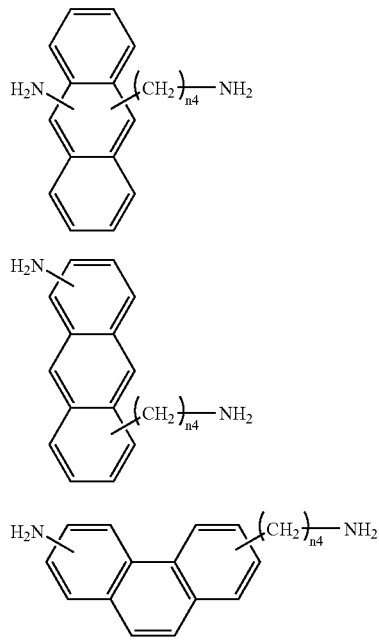
In the formulae [27] to [31], n4 is an integer of from 1 to 10. Further, in the formulae, one or more optional hydrogen atoms in the aromatic ring or the condensed ring may be substituted by a monovalent organic group other than an amino group.
Further, as specific examples, e.g. diamines of the formulae [32] to [49] may be mentioned.
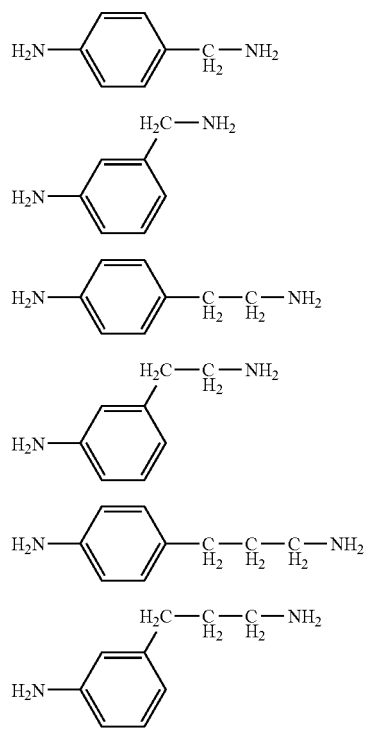
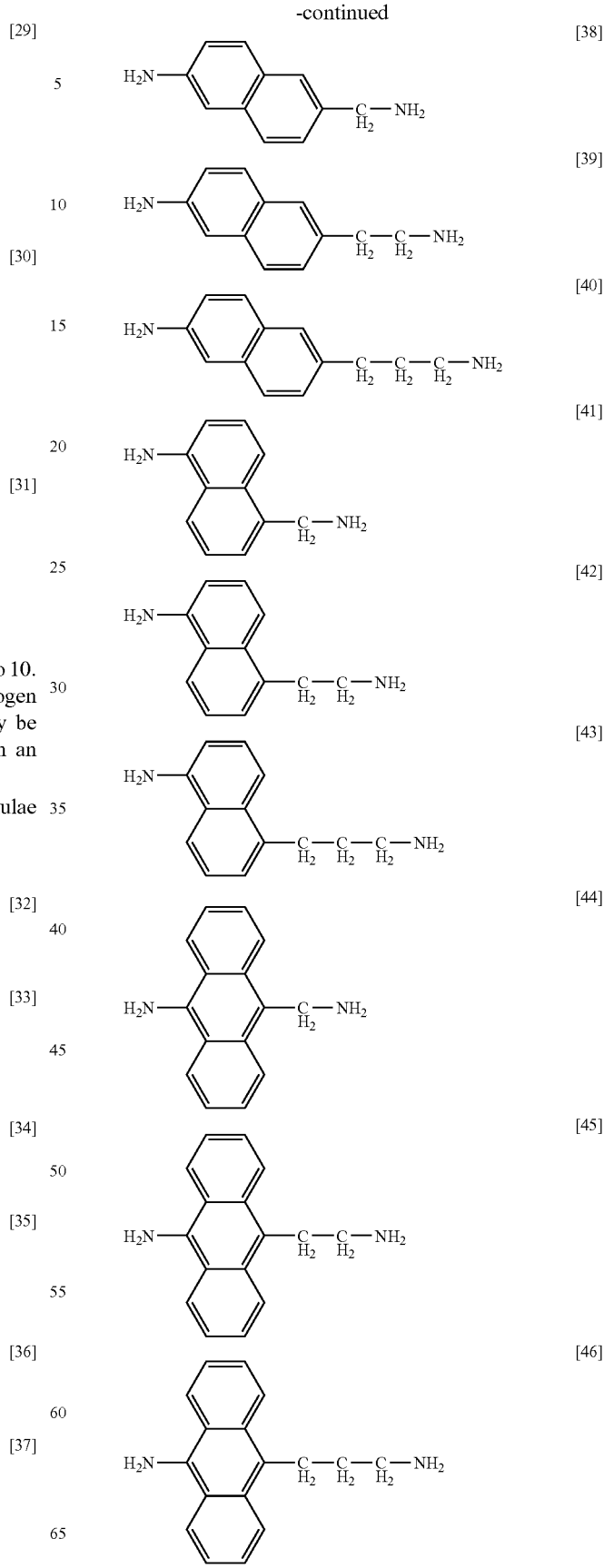

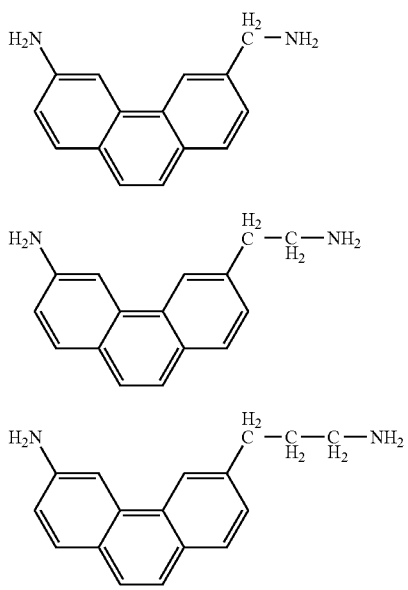

In the diamines represented by the above formulae [32] to [49], one or more optional hydrogen atoms in the benzene ring or the condensed ring may be substituted by a monovalent organic group other than an amino group. Further, as specific examples in the case of the condensed rings of the formulae [2-5] to [2-10], similar compounds in accordance with the cases of the formulae [2-1] to [2-4] may be mentioned.

Among the above diamines, preferred is a diamine wherein A is represented by the formula [2-1] or the formula [2-2]. Specifically, preferred are the formulae [6], [7], [10] to [28] and [32] to [43]. Preferred are diamines of the formulae [27] and [28] wherein n4 is an integer of from 1 to 6. More preferred are diamines represented by the formulae [32] to [43], which are diamines of the formulae [27] and [28] wherein n4 is an integer of from 1 to 3.

As the diamine component to be used in the present invention, it is possible to combine at least one of the above-described diamines represented by the formula [1] and one or more selected from other diamines. Examples of other diamines are mentioned below, but other diamines are not limited thereto.

Examples of an alicyclic diamine include 1,4-diaminocyclohexane, 1,3-diaminocyclohexane, 4,4'-diaminodicyclohexylmethane, 4,4'-diamino-3,3'-dimethyldicyclohexylamine and isophoronediamine. Examples of an aromatic diamine include o-, m-, p-phenylenediamine, diaminotoluenes (such as 2,4-diaminotoluene), 1,4-diamino-2,methoxybenzene, 2,5-diamino-p-xylene, 1,3-diamino-4-chlorobenzene, 3,5-diaminobenzoic acid, 1,4-diamino-2,5-dichlorobenzene, 4,4'-diamino-1,2-diphenylethane, 4,4'-diamino-2,2'-dimethylbibenzyl, 4,4'-diaminodiphenylmethane, 3,3'-diaminodiphenylmethane, 3,4'-diaminodiphenylmethane, 4,4'-diamino-3,3'-dimethyldiphenylmethane, 2,2'-diaminostilbene, 4,4'-diaminostilbene, 4,4'-diaminodiphenyl ether, 3,4'-diaminodiphenyl ether, 4,4'-diaminodiphenyl sulfide, 4,4'-diaminodiphenylsulfone, 3,3'-diaminodiphenylsulfone, 4,4'-diaminobenzophenone, 1,3-bis(3-aminophenoxy)benzene, 1,3-bis(4-aminophenoxy)benzene, 1,4-bis(4-aminophenoxy)benzene, 3,5-bis(4-aminophenoxy)benzoic acid, 4,4'-bis(4-aminophenoxy)bibenzyl, 2,2-bis[(4-aminophenoxy)methyl]propane, 2,2-bis[4-(4-aminophenoxy)phenyl]hexafluoropropane, 2,2-bis[4-(4-aminophenoxy)phenyl]propane, bis[4-(3-aminophenoxy)phenyl]sulfone, bis[4-(4-aminophenoxy)phenyl]sulfone, 1,1-bis(4-aminophenyl)cyclohexane, α,α'-bis(4-aminophenyl)-1,4-diisopropylbenzene, 9,9-bis(4-aminophenyl)fluorene, 2,2-bis(3-aminophenyl)hexafluoropropane, 2,2-bis(4-aminophenyl)hexafluoropropane, 4,4'-diaminodiphenylamine, 2,4-diaminodiphenylamine, 1,8-diaminonaphthalene, 1,5-diaminonaphthalene, 1,5-diaminoanthraquinone, 1,3-diaminopyrene, 1,6-diaminopyrene, 1,8-diaminopyrene, 2,7-diaminofluorene, 1,3-bis(4-aminophenyl)tetramethyldisiloxane, benzidine, 2,2'-dimethylbenzidine, 1,2-bis(4-aminophenyl)ethane, 1,3-bis(4-aminophenyl)propane, 1,4-bis(4-aminophenyl)butane, 1,5-bis(4-aminophenyl)pentane, 1,6-bis(4-aminophenyl)hexane, 1,7-bis(4-aminophenyl)heptane, 1,8-bis(4-aminophenyl)octane, 1,9-bis(4-aminophenyl)nonane, 1,10-bis(4-aminophenyl)decane, 1,3-bis(4-aminophenoxy)propane, 1,4-bis(4-aminophenoxy)butane, 1,5-bis(4-aminophenoxy)pentane, 1,6-bis(4-aminophenoxy)hexane, 1,7-bis(4-aminophenoxy)heptane, 1,8-bis(4-aminophenoxy)octane, 1,9-bis(4-aminophenoxy)nonane, 1,10-bis(4-aminophenoxy)decane, di(4-aminophenyl)propane-1,3-dioate, di(4-aminophenyl)butane-1,4-dioate, di(4-aminophenyl)pentane-1,5-dioate, di(4-aminophenyl)hexane-1,6-dioate, di(4-aminophenyl)heptane-1,7-dioate, di(4-aminophenyl)octane-1,8-dioate, di(4-aminophenyl)nonane-1,9-dioate, di(4-aminophenyl)decane-1,10-dioate, 1,3-bis[4-(4-aminophenoxy)phenoxy]propane, 1,4-bis[4-(4-aminophenoxy)phenoxy]butane, 1,5-bis[4-(4-aminophenoxy)phenoxy]pentane, 1,6-bis[4-(4-aminophenoxy)phenoxy]hexane, 1,7-bis[4-(4-aminophenoxy)phenoxy]heptane, 1,8-bis[4-(4-aminophenoxy)phenoxy]octane, 1,9-bis[4-(4-aminophenoxy)phenoxy]nonane and 1,10-bis[4-(4-aminophenoxy)phenoxy]decane.

Examples of a heterocyclic diamine include 2,6-diaminopyridine, 2,4-diaminopyridine, 2,4-diamino-1,3,5-triazine, 2,7-diaminodibenzofuran, 3,6-diaminocarbazole, 2,4-diamino-6-isopropyl-1,3,5-triazine and 2,5-bis(4-aminophenyl)-1,3,4-oxadiazole.

Further, examples of an aliphatic diamine include 1,2-diaminoethane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,3-diamino-2,2-dimethylpropane, 1,6-diamino-2,5-dimethylhexane, 1,7-diamino-2,5-dimethylheptane, 1,7-diamino-4,4-dimethylheptane, 1,7-diamino-3-methylheptane, 1,9-diamino-5-methylheptane, 1,12-diaminododecane, 1,18-diaminooctadecane and 1,2-bis(3-aminopropoxy)ethane.

Further, by use of a diamine having such a structure that an organic group known to have an effect of increasing the pretilt angle is bonded, such as a long chain alkyl group, a perfluoro group, an organic group having an aromatic cyclic substituent, an organic group having an aliphatic cyclic substituent or a steroid skeleton group, in combination, a liquid crystal aligning agent for a liquid crystal device (pretilt angle of from 4° to 6°) for TFT, a liquid crystal device (pretilt angel of from 4° to 8°) for STN, a liquid crystal device (pretilt angle of from 6° to 10°) for OCB and a liquid crystal device (pretilt angle of 90°) for VA can be obtained. Specific examples of such a diamine are mentioned below, but the diamine is not limited thereto.

In the following formula [50], j is an integer of from 5 to 20, and in the formulae [51] to [60] and [63] to [66], k is an integer of from 1 to 20.
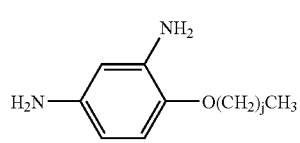
[50]
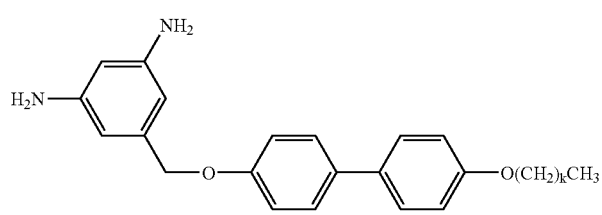
[51]
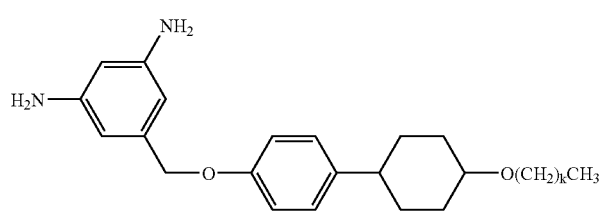
[52]
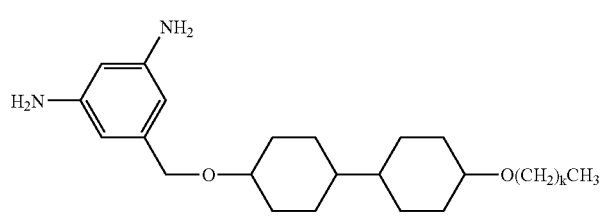
[53]
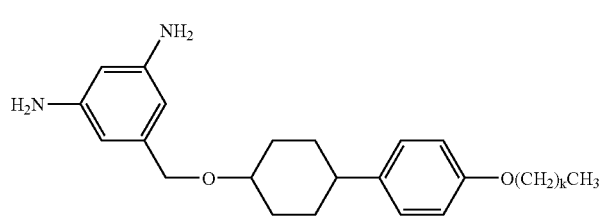
[54]
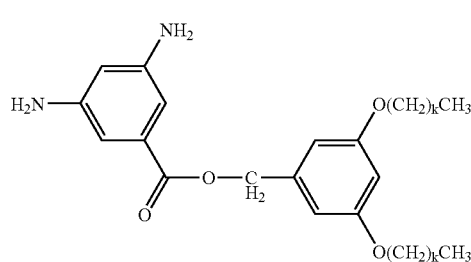
[55]
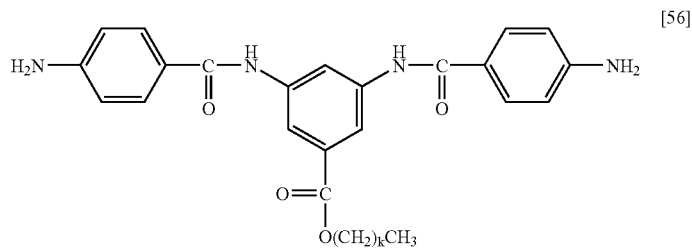
[56]

-continued
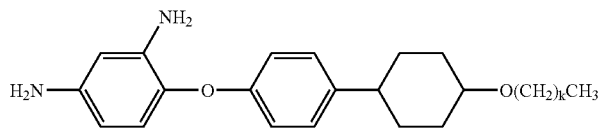
[57]
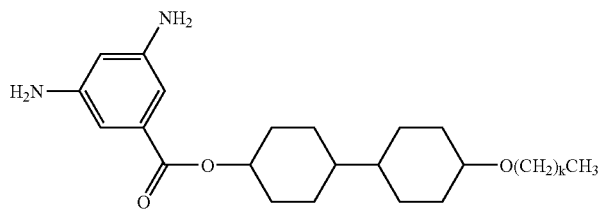
[58]
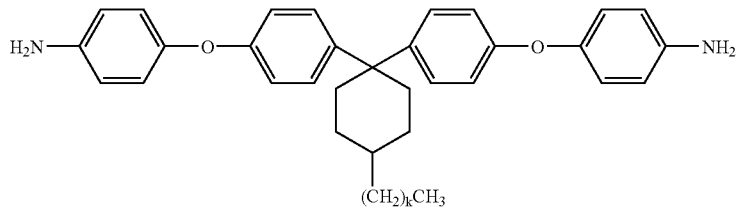
[59]
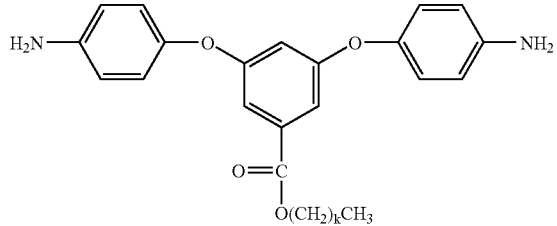
[60]
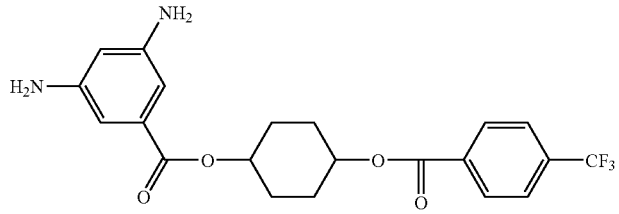
[61]
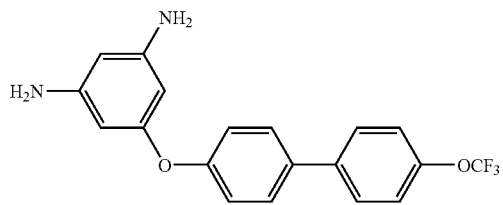
[62]
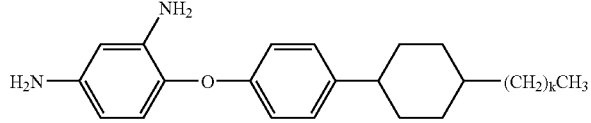
[63]
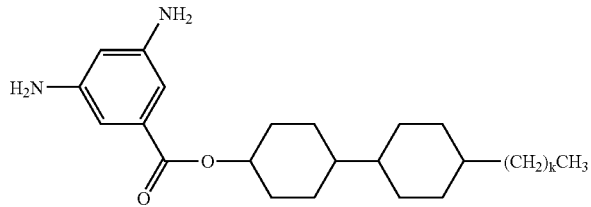
[64]

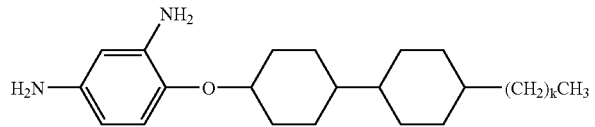
[65]
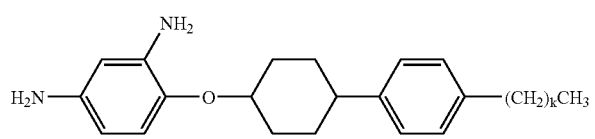
[66]
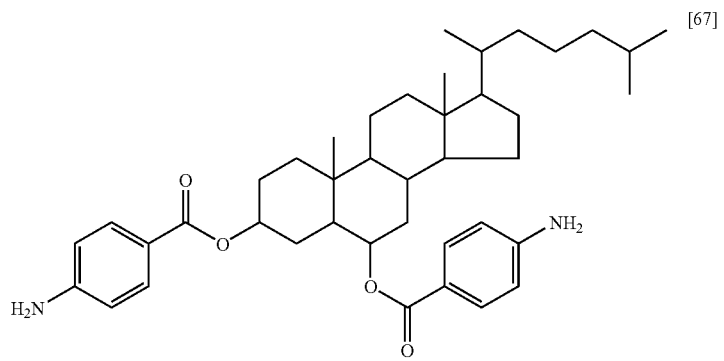
[67]
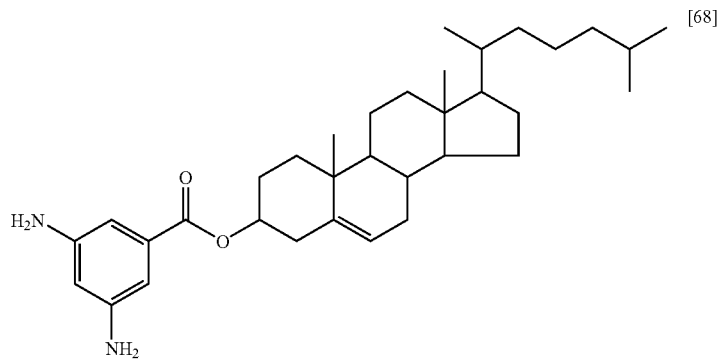
[68]
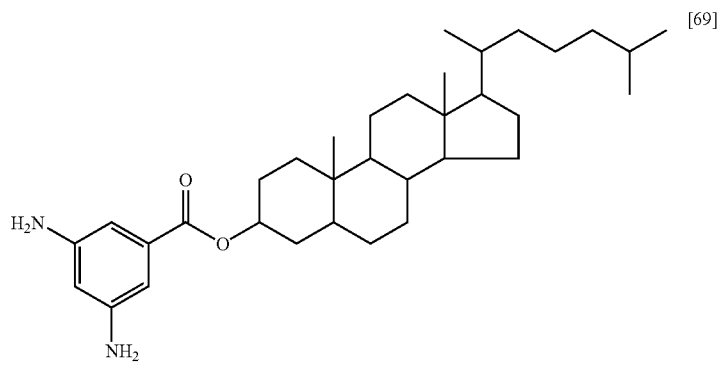
[69]

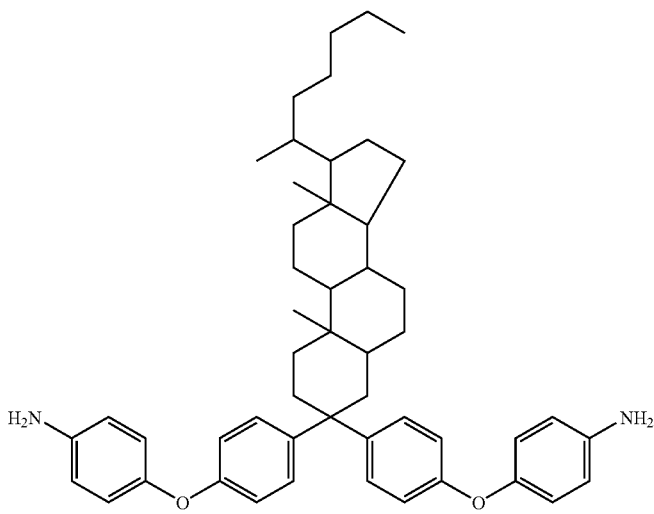

[70]

In the diamine component to be used for the liquid crystal aligning agent of the present invention, the diamine represented by the formula [1] is contained in an amount of at least 1 mol %, more preferably at least 10 mol %. If the proportion of the diamine represented by the formula [1] is too low, the liquid crystal aligning agent will be poor in the storage stability and the electrical characteristics in some cases.

The tetracarboxylic dianhydride component to be used in the present invention is not particularly limited. One, or two or more in combination selected from tetracarboxylic dianhydrides may be used. Specific examples are mentioned below, but the tetracarboxylic dianhydride component is not limited thereto.

Examples of one having an alicyclic structure or an aliphatic structure include 1,2,3,4-cyclobutanetetracarboxylic dianhydride, 1,2-dimethyl-1,2,3,4-cyclobutanetetracarboxylic dianhydride, 1,3-dimethyl-1,2,3,4-cyclobutanetetracarboxylic dianhydride, 1,2,3,4-tetramethyl-1,2,3,4-cyclobutanetetracarboxylic dianhydride, 1,2,3,4-cyclopentanetetracarboxylic dianhydride, 2,3,4,5-tetrahydrofurantetracarboxylic dianhydride, 1,2,4,5-cyclohexanetetracarboxylic dianhydride, 3,4-dicarboxy-1-cyclohexylsuccinic dianhydride, 3,4-dicarboxy-1,2,3,4-tetrahydro-1-naphthalenesuccinic dianhydride, 1, 2, 3, 4-butanetetracarboxylic dianhydride, bicyclo[3,3,0]octane-2,4,6,8-tetracarboxylic dianhydride, 3,3',4,4'-dicyclohexyltetracarboxylic dianhydride, 2,3,5-tricarboxycyclopentylacetic dianhydride, cis-3,7-dibutylcycloocta-1,5-diene-1,2,5,6-tetracarboxylic dianhydride, tricyclo[4.2.1.0$^{2,5}$]nonane-3,4,7,8-tetracarboxylic acid-3, 4:7,8-dianhydride and hexacyclo[6.6.0.12,7.03,6.19,14.010,13]hexadecane-4,5,11,12-tetracarboxylic acid-4, 5:11,12-dianhydride. Examples of an aromatic dianhydride include pyromellitic dianhydride, 3,3',4,4'-biphenyltetracarboxylic dianhydride, 2,2',3,3'-biphenyltetracarboxylic dianhydride, 2,3,3',4-biphenyltetracarboxylic dianhydride, 3,3',4,4'-benzophenonetetracarboxylic dianhydride, 2,3,3',4-benzophenonetetracarboxylic dianhydride, bis(3,4-dicarboxyphenyl)ether dianhydride, bis(3,4-dicarboxyphenyl)sulfonic dianhydride, 1,2,5,6-naphthalenetetracarboxylic dianhydride and 2,3,6,7-naphthalenetetracarboxylic diandydride.

It is preferred that at least 10 mol % of the tetracarboxylic dianhydride component is a tetracarboxylic dianhydride having an alicyclic structure or an aliphatic structure, whereby the voltage holding ratio will improve.

Preferred tetracarboxylic diandydrides having an alicyclic structure or an aliphatic structure include 1,2,3,4-cyclobutanetetracarboxylic dianhydride, 3,4-dicarboxy-1,2,3,4-tetrahydro-1-naphthalenesuccinic dianhydride, bicyclo[3,3,0]octane-2,4,6,8-tetracarboxylic dianhydride, 1,2,3,4-butanetetracarboxylic dianhydride and 2,3,5-tricarboxycyclopentylacetic dianhydride.

When at least 20 mol % of the tetracarboxylic dianhydride component is an aromatic dianhydride, the alignment of liquid crystal will improve, and the accumulated charge will decrease.

Preferred aromatic dianhydrides include pyromellitic dianhydride, 3,3',4,4'-biphenyltetracarboxylic dianhydride, 3,3',4,4'-benzophenonetetracarboxylic dianhydride and 1,4,5,8-naphthalenetetracarboxylic dianhydride.

The polymerization method of the tetracarboxylic dianhydride component with the diamine component to be used for the liquid crystal aligning agent of the present invention is not particularly limited. The components may be mixed in an organic solvent and thereby polymerized to form a polyamic acid, and this polyamic acid may be subjected to cyclodehydration to form a polyimide.

The method for mixing the tetracarboxylic dianhydride component and the diamine component in an organic solvent, may, for example, be a method wherein a solution having the diamine component dispersed or dissolved in an organic solvent, is stirred, and the tetracarboxylic dianhydride component is added as it is or as dispersed or dissolved in an organic solvent, or a method wherein, inversely, the diamine component is added to a solution having the tetracarboxylic dianhydride component dispersed or dissolved in an organic solvent, or a method wherein the tetracarboxylic dianhydride component and the diamine component are alternately added. Further, in a case where at least one of the tetracarboxylic dianhydride component and the diamine component is made of a plurality of compounds, such a plurality of compounds may be polymerized in a preliminarily mixed state or may individually sequentially be polymerized.

The temperature at the time of polymerization of the tetracarboxylic dianhydride component and the diamine component in an organic solvent, is usually from 0 to 150° C., preferably from 5 to 100° C., more preferably from 10 to 80° C. The higher the temperature is, the quicker the polymerization reaction finishes. However, if it is too high, a polymer having a high molecular weight may not sometimes be obtained. Further, the polymerization may be carried out at an optional concentration, but if the concentration is too low, it tends to be difficult to obtain a polymer having a high molecular weight, and if the concentration is too high, the viscosity of the reaction solution tends to be too high to carry out uniform stirring. Accordingly, it is preferably from 1 to 50 mass %, more preferably from 5 to 30 mass %. At the initial stage, the polymerization may be carried out at a high concentration and then, an organic solvent may be added.

The organic solvent to be used for the above reaction is not particularly limited so long as it is capable of dissolving the formed polyamic acid. However, specific examples may be N,N-dimethylformamide, N,N-dimethylacetamide, N-methyl-2-pyrrolidone, N-methylcaprolactam, dimethyl sulfoxide, tetramethylurea, pyridine, dimethylsulfone, hexamethylsulfoxide and γ-butyrolactone. These solvents may be used alone or as mixed. Further, even a solvent which is incapable of dissolving the polyamic acid may be used as mixed to the above solvent within a range not to precipitate the formed polyamic acid. Further, moisture in the organic solvent tends to impair the polymerization reaction and further may cause hydrolysis of the formed polyamic acid, and therefore, it is preferred to use the organic solvent as dehydrated and dried.

The ratio of the tetracarboxylic dianhydride component to the diamine component, to be used for the polymerization reaction for the polyamic acid is preferably from 1:0.8 to 1:1.2 by molar ratio. The closer the molar ratio to 1:1, the larger the molecular weight of the polyamic acid to be obtained. If the molecular weight of the polyamic acid is too small, the strength of the coating film thereby obtainable may sometimes be inadequate, and inversely, if the molecular weight of the polyamic acid is too large, the viscosity of the liquid crystal aligning agent thereby obtainable tends to be too high, whereby the operation efficiency at the time of forming a coated film or the uniformity of the coated film tends to be poor. Therefore, the weight average molecular weight of the polyamic acid to be used for the liquid crystal aligning agent of the present invention is preferably from 2,000 to 500,000, more preferably from 5,000 to 300,000.

The polyamic acid obtained as described above may be used as it is, as the liquid crystal aligning agent of the present invention, but may be subjected to cyclodehydration to obtain a polyimide, which may then be used. However, depending upon the structure of the polyamic acid, there may be a case wherein by the imidation reaction, it may be insolubilized and will be hardly useful as a liquid crystal aligning agent. In such a case, amic acid groups in the polyamic acid may not all be imidized, and it may be one imidized to such an extent where a proper solubility can be maintained.

The imidation reaction to cyclodehydrate the polyamic acid is usually thermal imidation wherein the solution of the polyamic acid is heated as it is, or chemical imidation wherein a catalyst is added to the solution of the polyamic acid. However, the chemical imidation wherein the imidation reaction proceeds at a relatively low temperature, is preferred, since decrease in the molecular weight of the polyimide to be obtained, is less likely to occur.

The chemical imidation can be carried out by stirring the polyamic acid in an organic solvent in the presence of a basic catalyst and an acid anhydride. The reaction temperature at that time is usually from −20 to 250° C., preferably from 0 to 180° C., and the reaction time may be from 1 to 100 hours. The amount of the basic catalyst is from 0.5 to 30 mols, preferably from 2 to 20 mols, per mol of the amic acid groups, and the amount of the acid anhydride is from 1 to 50 mols, preferably from 3 to 30 mols, per mol of amic acid groups. If the amount of the basic catalyst or the acid anhydride is too small, the reaction may not adequately proceed, and if it is too much, it tends to be difficult to completely remove it after completion of the reaction.

As the basic catalyst to be used at that time, pyridine, triethylamine, trimethylamine, tributylamine or trioctylamine may, for example, be mentioned, and among them, pyridine is preferred since it has a proper basicity to let the reaction proceed. Whereas, as the acid anhydride, acetic anhydride, trimellitic anhydride or pyromellitic anhydride may, for example, be mentioned, and among them, it is preferred to employ acetic anhydride, whereby purification after completion of the reaction will be easy. As the organic solvent, the above-mentioned solvent to be used for the polymerization reaction for the polyamic acid, may be used. The imidation rate by the chemical imidation may be controlled by adjusting the amount of the catalyst and the reaction temperature or the reaction time.

In a polyimide solution thus obtained, the added catalyst still remains in the solution. Accordingly, in order to use it for the liquid crystal aligning agent of the present invention, it is preferred that the polyimide solution is put into a poor solvent under stirring to precipitate and recover the polyimide. The poor solvent to be used for the precipitation and recovery of the polyimide is not particularly limited, and it may, for example, be methanol, acetone, hexane, butylcellosolve, heptane, methyl ethyl ketone, methyl isobutyl ketone, ethanol, toluene or benzene. The polyimide precipitated by being put into the poor solvent, may be recovered by filtration and washing and then dried under atmospheric pressure or reduced pressure at room temperature or under heating, to obtain a powder. The polyimide may be purified by repeating an operation of further dissolving this powder in a good solvent, followed by reprecipitation from 2 to 10 times. In a case where impurities can not be removed by a single operation of recovery by precipitation, it is preferred to carry out such a purification step. It is preferred to use, as the poor solvent, at least three types of poor solvents such as alcohols, ketones or hydrocarbons as mixed or sequentially, since it is thereby possible to further increase the efficiency for purification.

Further, the polyamic acid may also be recovered by precipitation and purified by a similar operation. In a case where it is desired not to have the solvent used for the polymerization of the polyamic acid incorporated in the liquid crystal aligning agent of the present invention or in a case where an unreacted monomer component or impurities are present in the reaction solution, this recovery by precipitation and purification may be carried out.

The liquid crystal aligning agent of the present invention is one containing at least one polymer selected from the polyamic acid as obtained above and the polyimide having such a polyamic acid cyclodehydrated, but usually used as a solution having such a polymer dissolved in an organic solvent. To obtain the liquid crystal aligning agent, the reaction solution of the polyamic acid or the polyimide may be used as it is, or one recovered by precipitation from the reaction solution may be re-dissolved in an organic solvent.

Such an organic solvent is not particularly limited so long as it is capable of dissolving the polymer to be contained. Specific examples thereof may be N,N-dimethylformamide, N,N-dimethylacetamide, N-methyl-2-pyrrolidone, N-methylcaprolactam, 2-pyrrolidone, N-ethylpyrrolidone, N-vinylpyrrolidone, dimethyl sulfoxide, tetramethylurea, pyridine, dimethylsulfone, hexamethylsulfoxide, γ-butyrolactone and 1,3-dimethyl-imidazolidinone. They may be used alone or in combination as a mixture of two or more of them.

Further, even a solvent which is incapable of dissolving the polymer alone may be mixed to the liquid crystal aligning agent of the present invention within a range not to let the polymer precipitate. Especially, it is possible to properly mix a solvent having a low surface tension, such as ethylcellosolve, butylcellosolve, ethylcarbitol, butylcarbitol, ethylcarbitol acetate, ethylene glycol, 1-methoxy-2-propanol, 1-ethoxy-2-propanol, 1-butoxy-2-propanol, 1-phenoxy-2-propanol, propylene glycol monoacetate, propylene glycol diacetate, propylene glycol-1-monomethyl ether-2-acetate, propylene glycol-1-monoethyl ether-2-acetate, dipropylene glycol, 2-(2-ethoxypropoxy)propanol, lactic acid methyl ester, lactic acid ethyl ester, lactic acid n-propyl ester, lactic acid n-butyl ester or lactic acid isoamyl ester. It is known that the uniformity of the coated film at the time of coating on the substrate will improve by mixing such a solvent, and the solvent is suitably used for the liquid crystal aligning agent of the present invention also.

The solid content concentration in the liquid crystal aligning agent of the present invention may suitably be changed depending upon the setting of the thickness of the liquid crystal alignment film to be formed, but it is preferably from 1 to 10 mass %. If it is less than 1 mass %, it tends to be difficult to form a coated film which is uniform and flawless, and if it is larger than 10 mass %, the storage stability of the solution may sometimes be poor.

Further, to the liquid crystal aligning agent of the present invention, in order to improve the adhesion of the coated film to the substrate, an additive such as a silane coupling agent may be added. Further, a polyamic acid or a polyimide other than the polymer of the present invention may be mixed, or a resin component other than the polymer, such as an acrylic resin, a polyurea, a polyamide or a polyurethane may be incorporated.

The liquid crystal aligning agent of the present invention obtained as described above, is subjected to filtration and then applied to a substrate, followed by drying and baking to form a coated film, and this coated film surface is subjected to alignment treatment such as rubbing or irradiation with light, so that it may be used as a liquid crystal alignment film.

As the substrate to be used at that time is not particularly limited so long as it is a highly transparent substrate, and it is possible to employ a glass substrate or a plastic substrate such as an acrylic substrate or a polycarbonate substrate. It is preferred to employ a substrate having ITO electrodes, etc. formed for liquid crystal driving with a view to simplification of the process. Further, in the case of a reflection type liquid crystal display device, an opaque material such as a silicon wafer may be used for a substrate for one side, and the electrodes in such a case may be made of a material which reflects lights, such as aluminum.

As the method for applying the liquid crystal aligning agent, a spin coating method, a printing method or an inkjet method may, for example, be mentioned. However, from the viewpoint of the productivity, a transfer printing method is industrially widely employed, and it may suitably be employed also for the liquid crystal aligning agent of the present invention.

The step of drying after application of the liquid crystal aligning agent is not necessarily required, but it is preferred to include a drying step in a case where the time after the application to the baking is not constant for every substrate or in a case where baking is not immediately carried out after the application. Such drying may be carried out until the solvent is evaporated to such an extent that the coated film shape will not be deformed by e.g. transportation of the substrate, and the drying means is not particularly limited. As a specific example, a method may be employed wherein drying is carried out for from 0.5 to 30 minutes, preferably from 1 to 5 minutes, on a hot plate of from 50 to 150° C., preferably from 80 to 120° C.

The baking of the substrate having the liquid crystal aligning agent applied thereto can be carried out at an optional temperature of from 100 to 350° C., preferably from 150 to 300° C., more preferably from 180 to 250° C. In a case where the liquid crystal aligning agent contains a polyamic acid, the conversion rate from the polyamic acid to the polyimide may change depending upon this baking temperature, but the liquid crystal aligning agent of the present invention is not required to be imidated 100%. However, it is preferred to carry out baking at a temperature higher by at least 10° C. than the heat treatment temperature such as curing of a sealing agent, which is required in the step of producing a liquid crystal cell.

The thickness of the coated film after baking is preferably from 5 to 300 nm, more preferably from 10 to 100 nm, since if it is too thick, such will be disadvantageous from the viewpoint of the power consumption of the liquid crystal display device, and if it is too thin, the reliability of the liquid crystal display device may sometimes decrease.

The liquid crystal display device of the present invention is one prepared in such a manner that a substrate provided with a liquid crystal alignment film is obtained from the liquid crystal aligning agent of the present invention by the above-described method, and then a liquid crystal cell is prepared by a known method to obtain a liquid crystal display device.

A process for producing the liquid crystal cell is not particularly limited, but as an example, a process is common wherein a pair of substrates having liquid crystal alignment films formed thereon are placed with a spacer interposed between the liquid crystal alignment film faces, so that the rubbing directions of the liquid crystal alignment films will be at an optional angle of from 0 to 270°, their periphery is fixed by a sealing agent, then liquid crystal is injected, followed by sealing. In this case, the spacer used is preferably from 1 to 30 μm, more preferably from 2 to 10 μm.

The method for sealing liquid crystal is not particularly limited, and it may, for example, be a vacuum method wherein liquid crystal is injected after reducing the pressure in the liquid crystal cell thus prepared, or a dropping method wherein liquid crystal is dropped, followed by sealing.

The liquid crystal display device prepared by using the liquid crystal aligning agent of the present invention, in such a manner, has excellent electrical characteristics and thus can be made to be a liquid crystal display device which is less susceptible to lowering of contrast or to image persistence. Thus, it is suitably employed for display devices of various systems employing nematic liquid crystal, such as a TN liquid crystal display device, an STN liquid crystal display device, a TFT liquid crystal display device, an OCB liquid crystal display device and further an in-plane switching liquid crystal display device or a vertically aligned liquid crystal display device. Further, by selecting the liquid crystal to be used, it may be used also for a ferroelectric or antiferroelectric liquid crystal display device.

Now, the present invention will be described in further detail with reference to Examples. However, it should be understood that the present invention is by no means restricted to such specific Examples.

EXAMPLES

Description of Abbreviations Used in the Present Examples (Tetracarboxylic Dianhydride)
CBDA: 1,2,3,4-Cyclobutanetetracarboxylic dianhydride
TDA: 3,4-Dicarboxy-1,2,3,4-tetrahydro-1-naphthalene-succinic dianhydride
PMDA: Pyromellitic dianhydride
(Diamine)
3-ABA: 3-Aminobenzylamine (formula [33])
4-ABA: 4-Aminobenzylamine (formula [32])
6-ANaMA: 6-Aminonaphthalenemethylamine (formula [38])
6-DAN: 2,6-Diaminonaphthalene
4-APhA: 2-(4-Aminophenyl)ethylamine (formula [34])
6-ANaEA: 2-(6-Aminonaphthalene)ethylamine (formula [39])
DADOB: 1,3-Diamino-4-dodecyloxybenzene
DAHOB: 1,3-Diamino-4-hexadecyloxybenzene
DAOOB: 1,3-Diamino-4-octadecyloxybenzene
p-PDA: p-Phenylenediamine
BAPB: 1,3-Bis(4-aminophenoxy)benzene
DDM: 4,4'-Diaminodiphenylmethane
BAPE: 1,2-Bis(4-aminophenyl)ethane
DAE: 1,2-Diaminoethane
DADPA: 4,4'-Diaminodiphenylamine
BAPP: 1,5-Bis(4-aminophenoxy)pentane
(Organic Solvent)
NMP: N-Methyl-2-pyrolidone
BCS: Butylcellosolve
GBL: γ-Butyrolactone
THL: Tetrahydrofuran
DMSO: Dimethyl sulfoxide
DMF: N,N-dimethylformamide
TFA: Trifluoroacetic acid
Et3N: Triethylamine
t-BuOH: t-Butanol
(Others)
DPPA: Diphenylphosphoryl azide
AcCl: Acetyl chloride
Boc: t-Butoxycarbonyl

Preparation Example 1

CBDA/4-ABA 18.83 g (0.096 mol) of CBDA and 12.22 g (0.1 mol) of 4-ABA were reacted in 279 g of NMP at room temperature for 5 hours to prepare a polyamic acid solution. The polymerization reaction proceeded easily and uniformly to obtain a solution of a polyamic acid having a number average molecular weight of 12,836 and a weight average molecular weight of 28,165. For measurement of the average molecular weights, a room temperature gel permeation chromatography (GPC) apparatus (SSC-7200) manufactured by Senshu Kagaku K.K. and Shodex columns (KD 803, 805) were used. For the measurement, TSK standard polyethylene oxides (molecular weight: about 900,000, 150,000, 100,000, 30,00) manufactured by TOSOH CORPORATION and polyethylene glycols (molecular weight: about 12,000, 4,000, 1,000) manufactured by Polymer Laboratories Ltd. were used as standard samples for calibration curve preparation to calculate the number average molecular weight and the weight average molecular weight. Further, to this solution, poor solvents BCS and NMP were added to adjust the polyamic acid concentration would be 5 mass % and the BCS concentration would be 20 mass %, to prepare a liquid crystal aligning agent.

Preparation Example 2

CBDA/3-ABA 19.22 g (0.098 mol) of CBDA and 12.22 g (0.1 mol) of 3-ABA were reacted in 283 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 28,114 and a weight average molecular weight of 45,429 was obtained. Further, to this solution, poor solvents BCS and NMP were added so that the polyamic acid concentration would be 5 mass % and the BCS concentration would be 20 mass % to prepare a liquid crystal aligning agent.

Preparation Example 3

CBDA/4-APhA 19.41 g (0.099 mol) of CBDA and 13.62 g (0.1 mol) of 4-APhA were reacted in 297 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 7,950 and a weight average molecular weight of 14,498 was obtained. Further, to this solution, poor solvents BCS and NMP were added so that the polyamic acid concentration would be 5 mass % and the BCS concentration would be 20 mass % to prepare a liquid crystal aligning agent.

Preparation Example 4

CBDA/6-ANaMA

6-Aminonaphthalenemethylamine (6-ANaMA) was prepared in the following scheme (S-1). Here, 6-aminonaphthalenemethylamine is a novel compound not disclosed in any literature.

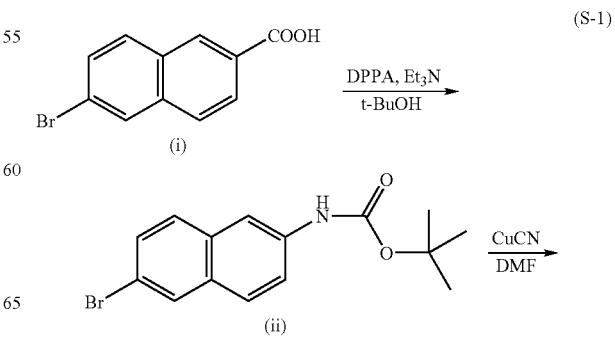

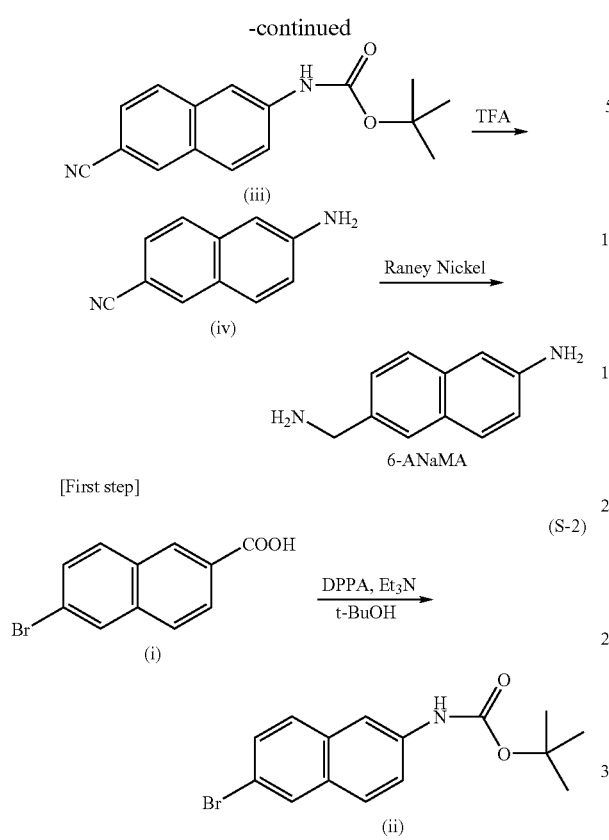

[First step]

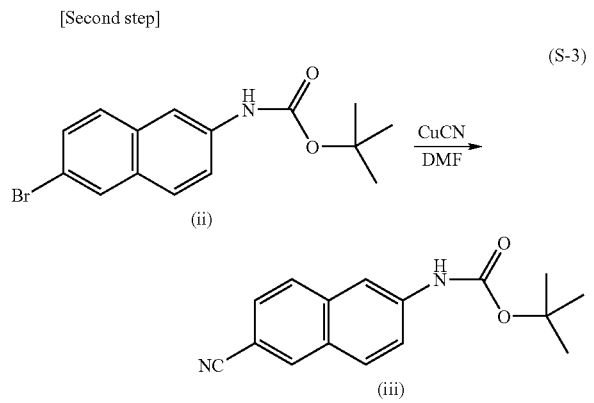

Compound (i) (55.0 g, 220 mmol), triethylamine (26.6 g, 260 mmol) and t-butanol (1,000 mL) were put in a 2 L four-necked flask made of glass in a stream of argon, followed by stirring at room temperature for dissolution. The internal temperature was increased to 50° C. 100 mL of diphenylphosphoryl azide (72.3 g, 260 mmol)/t-butanol was dropwise added thereto. After the dropwise addition, the internal temperature of the flask was increased to 75° C., followed by stirring for 4 hours. After standing to cool and filtration, the resulting filtrate was concentrated to obtain 153 g of a concentrated residue.

The concentrated residue was purified by column chromatography (adsorbent: silica gel, developing solvent: chloroform) to obtain compound (II) (56.2 g, yield: 79.5%).

[Second step]

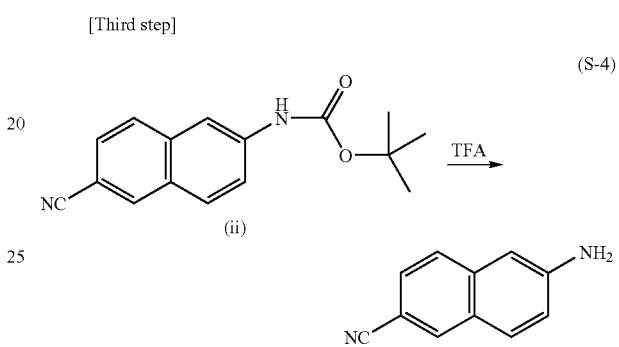

The compound (II) (56.2 g, 174 mmol) obtained in the above first step, dimethylformamide (220 mL) and copper cyanide (23.4 g, 261 mmol) were charged into a 1 L four-necked flask made of glass, and the internal temperature was increased to 85° C., followed by stirring for one hour. Then, stirring was carried out at a temperature of 100° C. for 2 hours and at a temperature of 145° C. for 4 hours. Then, the above solution was cooled to room temperature and poured into pure water (1,000 mL) to form precipitates. The precipitates were subjected to filtration, washed with water and dried. The dried product was purified by chromatography (adsorbent: NH silica gel, developing solvent: chloroform) to obtain compound (iii) (13.9 g, yield: 29.8 mass %).

[Third step]

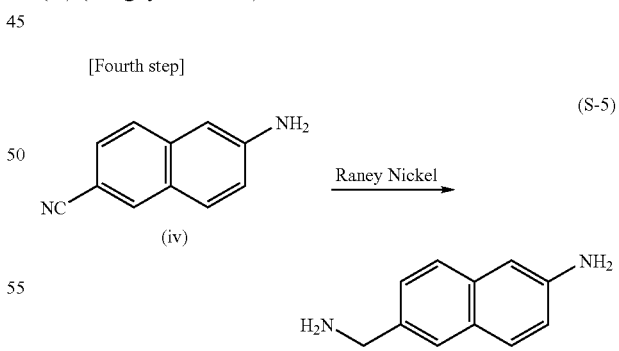

The compound (iii) (13.9 g, 51.8 mmol) and trifluoroacetic acid (50 mL) were charged into a 300 mL four-necked flask made of glass, followed by stirring at room temperature for dissolution. After stirring for 2 hours, the solution was cooled to a temperature of 5° C. or lower, and a 10% sodium hydroxide aqueous solution (150 mL) was added. Then, stirring was carried out for one hour, and the formed precipitates were subjected to filtration and dried. The dried product was purified by chromatography (adsorbent: NH silica gel, developing solvent: n-hexane/chloroform=1/1), and further purified by medium pressure column chromatography (adsorbent: ODS, mobile phase: 60% acetonitrile) to obtain compound (iv) (6.0 g, yield: 69%).

[Fourth step]

The compound (iv) (6.0 g, 35.7 mmol) obtained in the above fourth step, ethanol (100 mL), isopropyl alcohol (100 mL), a 28% ammonium water (16.7 mL) and Raney nickel (1.6 g) were charged into a 300 ml Teflon pressure container. The internal pressure was adjusted at 0.4 MPa by the hydrogen pressure to initiate catalytic hydrogenation reaction. After stirring at a temperature of 40° C. for 4 hours, filtration was carried out, and the filtrate was concentrated to obtain 6.6 g of a crude product. The crude product was purified by column chromatography (adsorbent: MH silica gel, developing solvent: chloroform→chloroform/methanol=1/1) to obtain 6-ANaMA (3.1 g, yield: 50%).

The obtained 6-ANaMA was identified by means of $^1$H-NMR (400 MHz, CDCl$_3$) and the results are shown below.

δ 7.63-7.55 (m, 3H), 7.33-7.31 (d, 1H), 6.69 (s, 1H), 6.94-6.92 (dd, 1H), 3.95 (s, 2H), 3.81 (s, 2H), 1.63 (s, 2H)

Then, 1.14 g (0.00582 mol) of CBDA and 1.03 g (0.006 mol) of 6-ANaMA obtained in the same manner as described above were reacted in 25 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 18,935 and a weight average molecular weight of 39,763 was obtained. Further, to this solution, poor solvents BCS and NMP were added so that the polyamic acid concentration would be 5 mass % and the BCS concentration would be 20 mass % to prepare a liquid crystal aligning agent.

Preparation Example 5

CBDA/6-ANaEA 2-(6-Aminonaphthalene)ethylamine (6-ANaEA) was prepared as follows. Here, 2-(6-aminonaphthalene)ethylamine is a novel compound not disclosed in any literature.

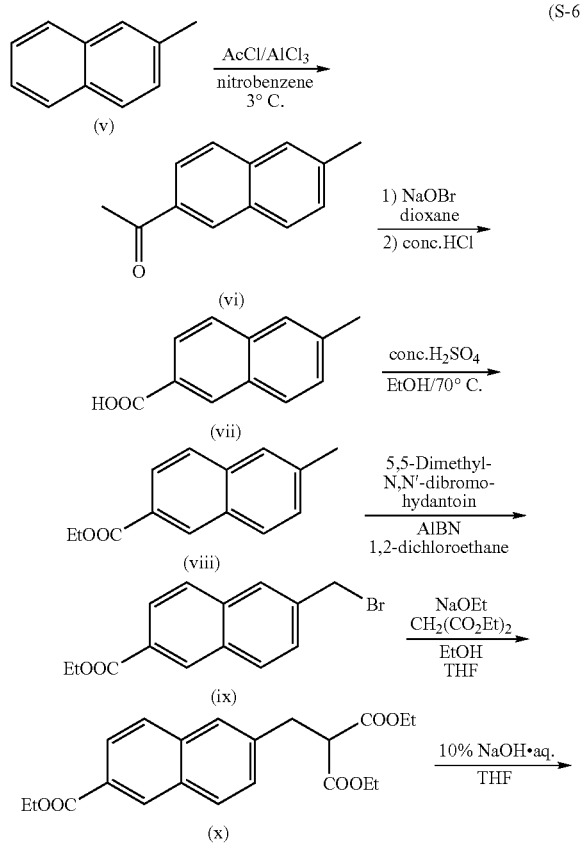

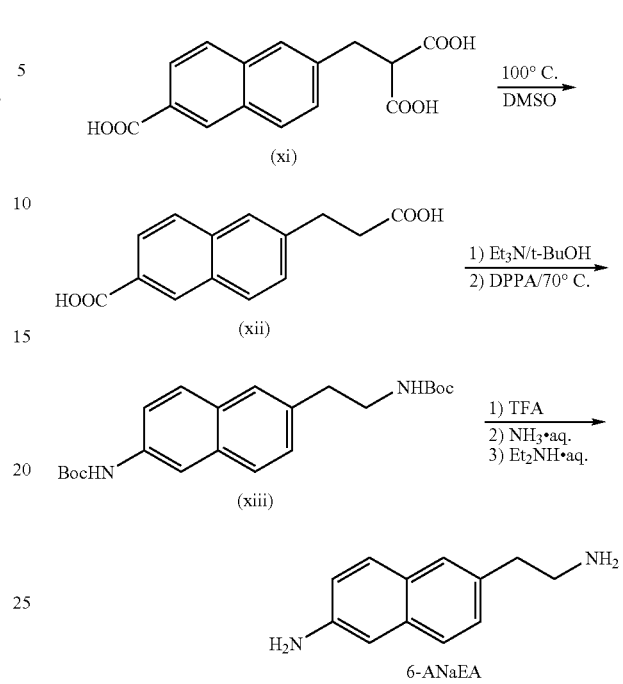

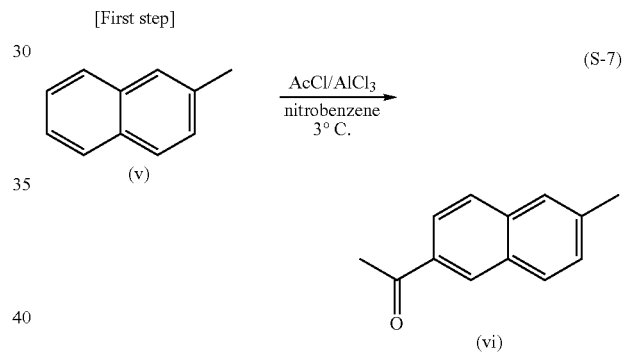

Aluminum chloride (147.6 g, 1.11 mol) and nitrobenzene (1,000 mL) were put in a 2 L round bottom flask made of glass in a stream of argon, followed by stirring at room temperature for dissolution. Acetyl chloride (79.0 mL, 1.11 mol) and nitrobenzene (500 mL) were added thereto, followed by stirring at room temperature for 20 minutes, and the solution was cooled with ice. The obtained solution will be referred to as solution P.

2-Methylnaphthalene (150 g, 1.01 mol) and nitrobenzene (750 mL) were added to a 3 L four-necked flask made of glass in a stream of argon and cooled with ice (temperature of 3° C.). The above prepared solution P was dropwise added thereto, followed by stirring at from 3 to 5° C. for one hour, and the solution was poured into ice water. Liquid-liquid separation was carried out, and the resulting organic layer and an extract from the aqueous layer with chloroform (300 mL×3) were put together and washed with pure water (500 mL), saturated sodium bicarbonate water (500 mL) and saturated salt solution (500 mL) in this order. After drying over anhydrous sodium sulfate, the product was concentrated to obtain a crude product (vi) (167 g), which was used for a second step as it was.

[Second step]

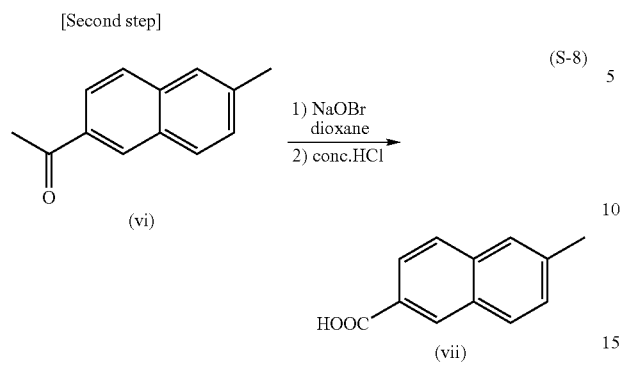

A 48% sodium hydroxide aqueous solution (302 g) and ice water (430 g) were charged to a 1 L round bottom flask made of glass, and under cooling with ice, bromine (190.1 g, 1.19 mol) was dropwise added thereto, followed by stirring for 30 minutes. The resulting solution will be referred to as solution Q.

The crude product (vi) (55 g, 299 mmol) obtained in the first step and 1,4-dioxane (760 mL) were charged to a 2 L four-necked flask made of glass and heated at 39° C., and the solution Q was dropwise added thereto. On that occasion, the reaction solution gradually generated heat. After completion of the dropwise addition, the reaction solution was stirred at 60° C. for 20 minutes and cooled with ice (4° C.). Concentrated hydrochloric acid (285 mL) was dropwise added thereto and then, sodium sulfite (74 g) was added, and the organic layer was extracted with THF (1,000 mL). The extract and an extract from the aqueous layer with THF (500 mL) were put together, and washed with saturated salt solution (300 mL×6), dried over anhydrous sodium sulfate and concentrated to obtain a crude product (97 g). The obtained crude product was subjected to slurry cleaning with chloroform to obtain compound (vii) (31 g, 167 mmol).

[Third step]

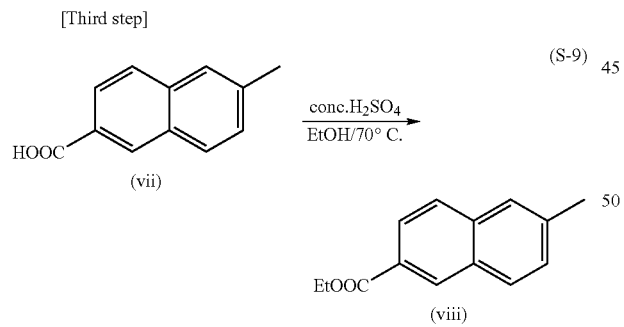

The compound (vii) (143 g, 0.77 mol) obtained in the second step and ethanol (2,000 mL) were charged into a 3 L four-necked flask made of glass, concentrated sulfuric acid (14 mL) was added, and the temperature was increased to 70° C. During the reaction, concentrated sulfuric acid was dividedly added twice in amounts of 6 mL and 20 mL, followed by stirring for 72 hours. The solution was cooled to room temperature and then concentrated, and ethyl acetate was added thereto. The solution thus obtained washed with saturated salt solution, saturated sodium bicarbonate water and saturated salt solution in this order, and the organic layer was dried over anhydrous sodium sulfate and concentrated to obtain a crude product (viii) (162 g, 86% purity), which was used for a fourth step as it was.

[Fourth step]

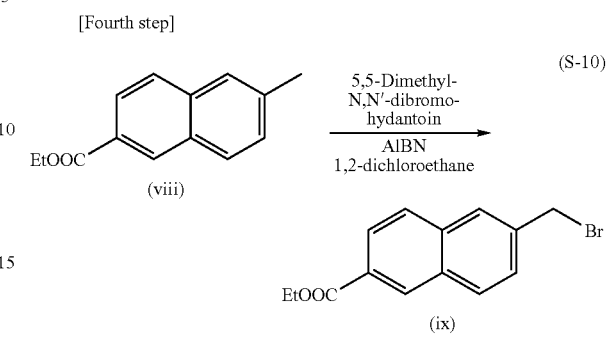

1,2-Dichloroethane (770 mL) was added to the crude product (viii) (154 g, 721 mmol) obtained in the third step for dissolution in a 2 L round bottom flask in a stream of argon. 5,5-Dimethyl-N,N'-dibromohydantoin (108 g, 377 mmol) and AIBN (629 mg, 0.6 mol %) were added thereto, followed by heating and reflux. After reflux for one hour, 5,5-dimethyl-N,N'-dibromohydantoin (10.8 g, 37.8 mmol) and AIBN (72.0 mg) were added, followed by reflux further for 2 hours. After cooling to room temperature, sodium sulfite (70 g), sodium bicarbonate (30 g) and pure water were added, and the aqueous layer and the organic layer were separated. Then, an extract from the aqueous layer with chloroform and the organic layer were put together, dried over anhydrous sodium sulfate and concentrated to obtain a crude product (ix) (231 g, 78% purity), which was used for a fifth step as it was.

[Fifth step]

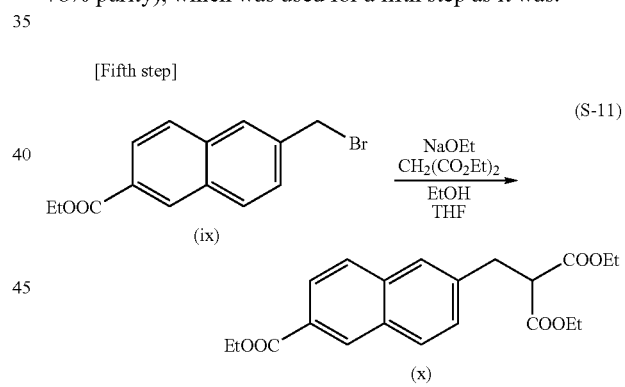

Ethanol (800 mL) was charged into a 2 L four-necked flask in a stream of argon, and metal sodium (20.0 g, 870 mmol) was added little by little thereto and dissolved. Then, diethyl malonate (132 mL, 869 mmol) was added thereto, followed by stirring at 50° C. for one hour. To this solution, a THF (500 mL) solution of the crude product (ix) (232 g, 791 mmol) obtained in the fourth step was dropwise added, followed by stirring at 70° C. for one hour. The solution was cooled to room temperature, pure water was added thereto, and then ethanol and THF were distilled off under reduced pressure. Chloroform (1,500 mL) was added thereto for extraction, and the extract washed with saturated salt solution, dried over anhydrous sodium sulfate and concentrated to obtain a crude product (302 g). The crude product was purified by column chromatography (adsorbent: silica gel, developing solvent: n-hexane/chloroform=1/1) to obtain compound (x) (205 g, 551 mmol, 70%).

[Sixth Step]

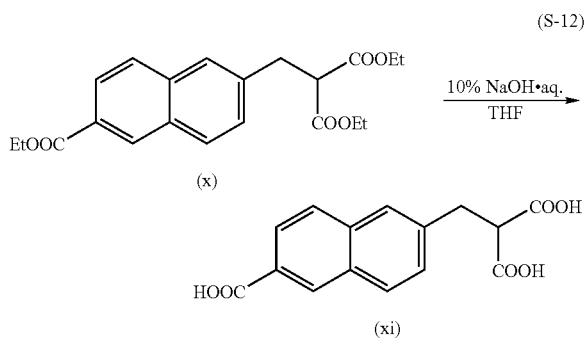

The compound (x) (205 g, 551 mmol) obtained in the fifth step and THF (400 mL) were charged into a 2 L four-necked flask, and a 10% sodium hydroxide aqueous solution (400 mL) was added thereto, followed by stirring at 57° C. for 3 hours. The solution was cooled with ice, concentrated hydrochloric acid (150 mL) and THF (500 mL) were added, followed by liquid-liquid separation, and the organic layer was taken out. The organic layer and extracts obtained by extraction from the aqueous layer twice with 200 mL of THF and with 100 mL of THF were put together, and washed with saturated salt solution, dried over anhydrous sodium sulfate and concentrated to obtain a crude product (xi) (215 g), which was used for a seventh step as it was.

[Seventh Step]

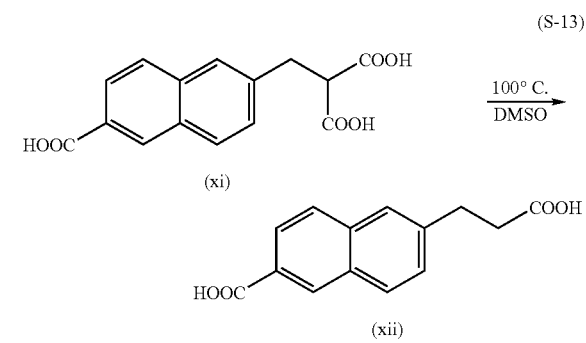

The crude product (x) (215 g) obtained in the sixth step and DMSO (1,000 mL) were charged into a 2 L round bottom flask, followed by stirring at 100° C. for one hour. The obtained solution was concentrated under reduced pressure and subjected to slurry cleaning with chloroform to obtain a compound (xii) (63 g, 256 mmol).

[Eight Step]

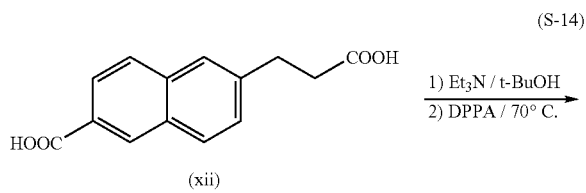

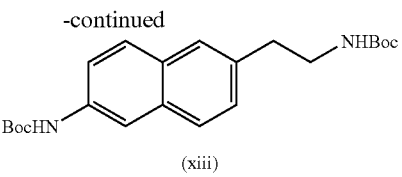

The compound (xii) (63 g, 256 mmol) obtained in the seventh step and t-butanol (2,000 mL) were charged into a 3 L four-necked flask in a stream of argon, and triethylamine (90 mL) was added thereto, followed by stirring for 30 minutes. DPPA (126 mL, 584 mmol) was added thereto, followed by reflux for 120 hours. The solution was concentrated under reduced pressure, and ethyl acetate and pure water were added thereto for extraction into the organic layer. The organic layer and an extract from the aqueous layer with chloroform were put together, and dried over anhydrous magnesium sulfate and concentrated to obtain a crude product (204 g). The crude product was purified by column chromatography (adsorbent: silica gel, developing solvent: chloroform/ethyl acetate=50/1→10/1) and further recrystallized from methanol to obtain compound (xiii) (61 g, 159 mmol, 61%).

[Ninth Step]

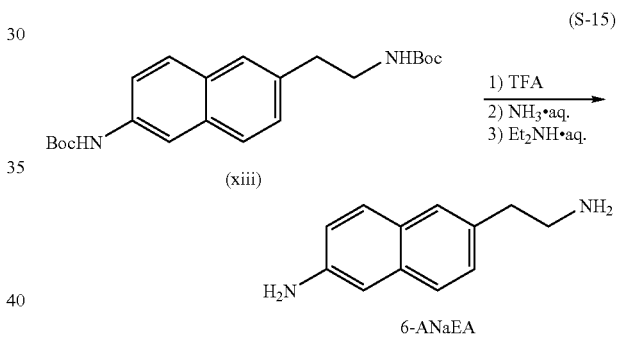

The compound (xiii) (31 g, 81 mmol) obtained in the eighth step was charged into a 500 mL round bottom flask, and trifluoroacetic acid (150 mL) was added thereto under cooling with ice. The solution was concentrated under reduced pressure, and pure water (200 mL) was added thereto, and under cooling with ice, concentrated ammonia water (50 mL) was added thereto, and precipitated solids were subjected to filtration. The obtained solids were suspended in deionized water (250 mL), and diethylamine (10 mL) was added thereto, followed by stirring at room temperature for 2 hours, and then the solids were subjected to filtration and dried under reduced pressure (60° C., 1 mmHg) to obtain a crude product (16.5 g). Further, the crude product was suspended in deionized water (200 mL), and diethylamine (10 mL) was added thereto, followed by stirring at room temperature for 2 hours, and then the solids were subjected to filtration and dried under reduced pressure (60° C., 1 mmHg) to obtain 6-ANaEA (13.5 g, 72 mmol, 89%).

The obtained 6-ANaEA was identified by means of $^1$HNMR (DMSO-d6) and $^{13}$CNMR (DMSO-d6), and the results are shown below.

$^1$HNMR (DMSO-d6) δ 7.50 (d, J=8.8 Hz, 1H), 7.41 (d, J=8.8 Hz, 1H), 7.40 (s, 1H), 7.13 (dd, J=8.8, 2.0 Hz, 1H), 6.89 (dd, J=8.8, 2.0 Hz, 1H), 6.77 (d, J=8.8, 2.0 Hz, 1H); $^{13}$CNMR (DMSO-d6) δ 146.0, 133.5, 132.6, 128.0, 127.5, 126.4, 125.1, 118.4, 105.9, 44.0, 40.3; MS (MALDI-TOF) 185.8

Then, 1.14 g (0.00582 mol) of CBDA and 1.12 g (0.006 mol) of the prepared 6-ANaEA were reacted in 26 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 20,885 and a weight average molecular weight of 38,924 was obtained. Further, to this solution, poor solvents BCS and NMP were added so that the polyamic acid concentration would be 5 mass % and the BCS concentration would be 20 mass % to prepare a liquid crystal aligning agent.

Preparation Example 6

TDA/6-ANaMA 1.78 g (0.00594 mol) of TDA and 1.03 g (0.006 mol) of 6-ANaMA were reacted in 32 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 10,432 and a weight average molecular weight of 19,820 was obtained. Further, to this solution, poor solvents BCS and NMP were added so that the polyamic acid concentration would be 5 mass % and the BCS concentration would be 20 mass % to prepare a liquid crystal aligning agent.

Preparation Example 7

TDA/6-ANaEA 1.78 g (0.00594 mol) of TDA and 1.12 g (0.006 mol) of 6-ANaEA were reacted in 33 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 9,441 and a weight average molecular weight of 15,860 was obtained. Further, to this solution, poor solvents BCS and NMP were added so that the polyamic acid concentration would be 5 mass % and the BCS concentration would be 20 mass % to prepare a liquid crystal aligning agent.

Preparation Example 8

CBDA/p-PDA, 4-ABA (50)

19.02 g (0.097 mol) of CBDA, 5.41 g (0.05 mol) of p-PDA and 6.11 g (0.05 mol) of 4-ABA were reacted in 275 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 11,322 and a weight average molecular weight of 21,775 was obtained. Further, to this solution, poor solvents BCS and NMP were added so that the polyamic acid concentration would be 5 mass % and the BCS concentration would be 20 mass % to prepare a liquid crystal aligning agent.

Preparation Example 9

CBDA/p-PDA, 6-ANaMA (50)

1.47 g (0.00752 mol) of CBDA, 0.43 g (0.004 mol) of p-PDA and 0.69 g (0.004 mol) of 6-ANaMA were reacted in 30 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 41,427 and a weight average molecular weight of 86,996 was obtained. Further, to this solution, poor solvents BCS and NMP were added so that the polyamic acid concentration would be 5 mass % and the BCS concentration would be 20 mass % to prepare a liquid crystal aligning agent.

Preparation Example 10

CBDA/p-PDA, 6-ANaEA (50)

1.49 g (0.0076 mol) of CBDA, 0.43 g (0.004 mol) of p-PDA and 0.75 g (0.004 mol) of 6-ANaEA were reacted in 30.7 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 52,727 and a weight average molecular weight of 109,181 was obtained. Further, to this solution, poor solvents BCS and NMP were added so that the polyamic acid concentration would be 5 mass % and the BCS concentration would be 20 mass % to prepare a liquid crystal aligning agent.

Preparation Example 11

CBDA/4-ABA, DADOB (20)

19.22 g (0.098 mol) of CBDA, 9.77 g (0.08 mol) of 4-ABA and 5.85 g (0.02 mol) of DADOB were reacted in 197 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 13,557 and a weight average molecular weight of 26,993 was obtained.

Further, to this solution, poor solvents BCS and NMP were added so that the polyamic acid concentration would be 5 is mass % and the BCS concentration would be 20 mass % to prepare a liquid crystal aligning agent.

Preparation Example 12

CBDA/p-PDA, 3-ABA (10)

18.63 g (0.095 mol) of CBDA, 9.73 g (0.09 mol) of p-PDA and 1.22 g (0.01 mol) of 3-ABA were reacted in 266 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 15,867 and a weight average molecular weight of 34,665 was obtained. Further, to this solution, poor solvents BCS and NMP were added so that the polyamic acid concentration would be 5 mass % and the BCS concentration would be 20 mass % to prepare a liquid crystal aligning agent.

Preparation Example 13

TDA/4-ABA (SPI)

29.73 g (0.099 mol) of TDA and 12.22 g (0.1 mol) of 4-ABA were reacted in 238 g of NMP at room temperature for 24 hours to prepare a polyamic acid solution. 50 g of the polyamic acid solution was diluted to 5 mass % with NMP, and 18.1 g of acetic anhydride and 8.4 g of pyridine as imidiation catalysts were added thereto, followed by reaction at 40° C. for 3 hours to prepare a soluble polyimide resin solution. This solution was poured into 0.6 L of methanol, and the obtained precipitates were collected by filtration and dried to obtain a white soluble polyimide (SPI) resin. The molecular weights of the obtained soluble polyimide were measured in the same manner as in Preparation Example 1 and as a result, the number average molecular weight was 8,127 and the weight average molecular weight was 14,284. 1 g of this powder was dissolved in 15 g of NMP and 4 g of BCS to prepare a soluble polyimide solution having a soluble polyimide concentration of 5 mass % and a BCS concentration of 20 mass % to obtain a liquid crystal aligning agent.

Preparation Example 14

TDA/4-APhA (SPI)

30.03 g (0.1 mol) of TDA and 13.62 g (0.1 mol) of 4-APhA were reacted in 247 g of NMP at room temperature for 24 hours to prepare a polyamic acid solution. 50 g of the polyamic acid solution was diluted to 5 mass % with NMP, and 17.5 g of acetic anhydride and 8.2 g of pyridine as imidiation catalysts were added thereto, followed by reaction at 40° C. for 3 hours to prepare a soluble polyimide resin solution. This solution was poured into 0.6 L of methanol, and the obtained precipitates were collected by filtration and dried to obtain a white soluble polyimide (SPI) resin. The molecular weights of the obtained soluble polyimide were measured in the same manner as in Preparation Example 1 and as a result, the number average molecular weight was 6,255 and the weight average molecular weight was 15,638. 1 g of this powder was dissolved in 15 g of NMP and 4 g of BCS to prepare a soluble polyimide solution having a soluble polyimide concentration of 5 mass % and a BCS concentration of 20 mass % to obtain a liquid crystal aligning agent.

Preparation Example 15

CBDA, TDA (20)/3-ABA, DADOB (10) (SPI)

15.49 g (0.079 mol) of CBDA, 6.01 g (0.02 mol) of TDA and 11.00 g (0.09 mol) of DADOB were reacted in 201 g of NMP at room temperature for 24 hours to prepare a polyamic acid solution. 50 g of the polyamic acid solution was diluted to 5 mass % with NMP, and 21.5 g of acetic anhydride and 10.0 g of pyridine as imidiation catalysts were added thereto, followed by reaction at 40° C. for 3 hours to prepare a soluble polyimide resin solution. This solution was poured into 0.6 L of methanol, and the obtained precipitates were collected by filtration and dried to obtain a white soluble polyimide (SPI) resin. The molecular weights of the obtained soluble polyimide were measured in the same manner as in Preparation Example 1 and as a result, the number average molecular weight was 5,145 and the weight average molecular weight was 12,297. 1 g of this powder was dissolved in 15 g of NMP and 4 g of BCS to prepare a soluble polyimide solution having a soluble polyimide concentration of 5 mass % and a BCS concentration of 20 mass % to obtain a liquid crystal aligning agent.

Preparation Example 16

PMDA/4-ABA 21.37 g (0.098 mol) of PMDA and 12.22 g (0.1 mol) of 4-ABA were reacted in 246 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 11,552 and a weight average molecular weight of 21,936 was obtained. Further, to this solution, poor solvents BCS and NMP were added so that the polyamic acid concentration would be 5 mass % and the BCS concentration would be 20 mass % to prepare a liquid crystal aligning agent.

Preparation Example 17

PMDA/3-ABA 21.59 g (0.099 mol) of PMDA and 12.22 g (0.1 mol) of 3-ABA were reacted in 248 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 11,922 and a weight average molecular weight of 18,111 was obtained. Further, to this solution, poor solvents BCS and NMP were added so that the polyamic acid concentration would be 5 mass % and the BCS concentration would be 20 mass % to prepare a liquid crystal aligning agent.

Preparation Example 18

PMDA/4-APhA 21.59 g (0.099 mol) of PMDA and 13.62 g (0.1 mol) of 4-APhA were reacted in 258 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 9,645 and a weight average molecular weight of 17,114 was obtained. Further, to this solution, poor solvents BCS and NMP were added so that the polyamic acid concentration would be 5 mass % and the BCS concentration would be 20 mass % to prepare a liquid crystal aligning agent.

Preparation Example 19

PMDA/6-ANaMA 0.85 g (0.00388 mol) of PMDA and 0.69 g (0.004 mol) of 6-ANaMA were reacted in 17.7 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 22,359 and a weight average molecular weight of 40,162 was obtained. Further, to this solution, poor solvents BCS and NMP were added so that the polyamic acid concentration would be 5 mass % and the BCS concentration would be 20 mass % to prepare a liquid crystal aligning agent.

Preparation Example 20

PMDA/6-ANaEA 0.85 g (0.00388 mol) of PMDA and 0.75 g (0.004 mol) of 6-ANaEA were reacted in 18.3 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 21,059 and a weight average molecular weight of 37,508 was obtained. Further, to this solution, poor solvents BCS and NMP were added so that the polyamic acid concentration would be 5 mass % and the BCS concentration would be 20 mass % to prepare a liquid crystal aligning agent.

Preparation Example 21

CBDA, PMDA (50)/4-ABA 9.81 g (0.05 mol) of CBDA, 10.36 g (0.0475 mol) of PMDA and 12.22 g (0.1 mol) of 4-ABA were reacted in 184 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 16,335 and a weight average molecular weight of 39,424 was obtained. Further, to this solution, poor solvents BCS and NMP were added so that the polyamic acid concentration would be 5 mass % and the BCS concentration would be 20 mass % to prepare a liquid crystal aligning agent.

Preparation Example 22

CBDA, PMDA (80)/4-ABA 3.92 g (0.02 mol) of CBDA, 16.79 g (0.077 mol) of PMDA and 12.22 g (0.1 mol) of 4-ABA were reacted in 187 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 13,937 and a weight average molecular weight of 25,928 was obtained. Further, to this solution, poor solvents BCS and NMP were added so that the polyamic acid concentration would be 5 mass % and the BCS concentration would be 20 mass % to prepare a liquid crystal aligning agent.

Preparation Example 23

CBDA, PMDA (80)/3-ABA 3.92 g (0.02 mol) of CBDA, 17.23 g (0.079 mol) of PMDA and 12.22 g (0.1 mol) of 3-ABA were reacted in 189 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 17,695 and a weight average molecular weight of 28,721 was obtained. Further, to this solution, poor solvents BCS and NMP were added so that the polyamic acid concentration would be 5 mass % and the BCS concentration would be 20 mass % to prepare a liquid crystal aligning agent.

Preparation Example 24

CBDA, PMDA (80)/4-APhA 3.92 g (0.02 mol) of CBDA, 16.79 g (0.077 mol) of PMDA and 13.62 g (0.1 mol) of 4-APhA were reacted in 195 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 10,268 and a weight average molecular weight of 19,672 was obtained. Further, to this solution, poor solvents BCS and NMP were added so that the polyamic acid concentration would be 5 mass % and the BCS concentration would be 20 mass % to prepare a liquid crystal aligning agent.

Preparation Example 25

CBDA, PMDA (80)/6-ANaMA 0.24 g (0.0012 mol) of CBDA, 0.97 g (0.00468 mol) of PMDA and 1.03 g (0.006 mol) of 6-ANaMA were reacted in 25.7 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 22,329 and a weight average molecular weight of 42,648 was obtained. Further, to this solution, poor solvents BCS and NMP were added so that the polyamic acid concentration would be 5 mass % and the BCS concentration would be 20 mass % to prepare a liquid crystal aligning agent.

Preparation Example 26

CBDA, PMDA (80)/6-ANaEA 0.24 g (0.02 mol) of CBDA, 0.97 g (0.074 mol) of PMDA and 1.12 g (0.1 mol) of 6-ANaEA were reacted in 26.7 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 20,124 and a weight average molecular weight of 34,211 was obtained. Further, to this solution, poor solvents BCS and NMP were added so that the polyamic acid concentration would be 5 mass % and the BCS concentration would be 20 mass % to prepare a liquid crystal aligning agent.

Preparation Example 27

CBDA, PMDA (80)/DDM, 4-ABA (50)

3.92 g (0.02 mol) of CBDA, 16.90 g (0.0775 mol) of PMDA, 9.91 g (0.05 mol) of DDM and 6.11 g (0.05 mol) of 4-ABA were reacted in 209 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 15,092 and a weight average molecular weight of 29,672 was obtained. Further, to this solution, poor solvents BCS and NMP were added so that the polyamic acid concentration would be 5 mass % and the BCS concentration would be 20 mass % to prepare a liquid crystal aligning agent.

Preparation Example 28

CBDA, PMDA (80)/DDM, 4-ABA (10)

3.92 g (0.02 mol) of CBDA, 17.01 g (0.078 mol) of PMDA, 1.22 µg (0.01 mol) of 4-ABA and 17.84 g (0.09 mol) of DDM were reacted in 227 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 16,881 and a weight average molecular weight of 36,179 was obtained. Further, to this solution, poor solvents BCS and NMP were added so that the polyamic acid concentration would be 5 mass % and the BCS concentration would be 20 mass % to prepare a liquid crystal aligning agent.

Preparation Example 29

CBDA, PMDA (80)/DDM, 6-ANaMA (10)

0.24 g (0.0012 mol) of CBDA, 1.01 g (0.00468 mol) of PMDA, 1.07 g (0.0054 mol) of DDM and 0.10 g (0.0006 mol) of 6-ANaMA were reacted in 28 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 22,778 and a weight average molecular weight of 52,389 was obtained. Further, to this solution, poor solvents BCS and NMP were added so that the polyamic acid concentration would be 5 mass % and the BCS concentration would be 20 mass % to prepare a liquid crystal aligning agent.

Preparation Example 30

CBDA, PMDA (80)/DDM, 6-ANaEA (10)

0.24 g (0.0012 mol) of CBDA, 1.02 g (0.078 mol) of PMDA, 1.07 g (0.0054 mol) of DDM and 0.11 g (0.0006 mol) of 6-ANaEA were reacted in 28.4 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 25,778 and a weight average molecular weight of 55,165 was obtained. Further, to this solution, poor solvents BCS and NMP were added so that the polyamic acid concentration would be 5 mass % and the BCS concentration would be 20 mass % to prepare a liquid crystal aligning agent.

Preparation Example 31

CBDA, PMDA (80)/BAPB, 4-ABA (70)

3.92 g (0.02 mol) of CBDA, 17.01 g (0.078 mol) of PMDA, 8.55 g (0.07 mol) of 4-ABA and 8.77 g (0.03 mol) of BAPB were reacted in 217 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 10,732 and a weight average molecular weight of 19,902 was obtained. Further, to this solution, poor solvents BCS and NMP were added so that the polyamic acid concentration would be 5 mass % and the BCS concentration would be 20 mass % to prepare a liquid crystal aligning agent.

Preparation Example 32

PMDA/4-ABA, DAHOB (10)

20.94 g (0.096 mol) of PMDA, 11.00 g (0.09 mol) of 4-ABA and 3.49 g (0.01 mol) of DAHOB were reacted in 201 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 7,038 and a weight average molecular weight of 12,695 was obtained. Further, to this solution, poor solvents BCS and NMP were added so that the polyamic acid concentration would be 5 mass % and the BCS concentration would be 20 mass % to prepare a liquid crystal aligning agent.

Preparation Example 33

CBDA, PMDA (80)/4-ABA, DADPA (30), BAPP (10)

3.92 g (0.02 mol) of CBDA, 17.01 g (0.078 mol) of PMDA, 7.33 g (0.06 mol) of 4-ABA, 5.98 g (0.03 mol) of DADPA and 2.86 g (0.01 mol) of BAPP were reacted in 210 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 12,080 and a weight average molecular weight of 29,113 was obtained. Further, to this solution, poor solvents BCS and NMP were added so that the polyamic acid concentration would be 5 mass % and the BCS concentration would be 20 mass % to prepare a liquid crystal aligning agent.

Preparation Example 34

CBDA, PMDA (80)/4-ABA, p-PDA (50)

3.92 g (0.02 mol) of CBDA, 16.58 g (0.076 mol) of PMDA, 6.11 g (0.05 mol) of 4-ABA and 5.41 g (0.05 mol) of p-PDA were reacted in 288 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 13,979 and a weight average molecular weight of 30,055 was obtained. Further, to this solution, poor solvents BCS and NMP were added so that the polyamic acid concentration would be 5 mass % and the BCS concentration would be 20 mass % to prepare a liquid crystal aligning agent.

Preparation Example 35

CBDA, PMDA (80)/4-ABA, BAPB (10)

3.92 g (0.02 mol) of CBDA, 17.01 g (0.078 mol) of PMDA, 11.00 g (0.09 mol) of 4-ABA and 2.92 g (0.01 mol) of BAPB were reacted in 198 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 11,943 and a weight average molecular weight of 24,961 was obtained. Further, to this solution, poor solvents BCS and NMP were added so that the polyamic acid concentration would be 5 mass % and the BCS concentration would be 20 mass % to prepare a liquid crystal aligning agent.

Preparation Example 36

PMDA/4-ABA:CBDA/4-ABA=8:2

20 Mass % of the liquid crystal aligning agent prepared in Preparation Example 1 and 80 mass % of the liquid crystal aligning agent prepared in Preparation Example 16 were blended to obtain a liquid crystal aligning agent.

Preparation Example 37

TDA/p-PDA, DAOOB (10) (SPI)

30.03 g (0.1 mol) of TDA, 9.73 g (0.09 mol) of p-PDA and 3.77 g (0.01 mol) of DAOOB were reacted in 247 g of NMP at 50° C. for 24 hours to prepare a polyamic acid solution. 50 g of the polyamic acid solution was diluted to 5 mass % with NMP, and 17.6 g of acetic anhydride and 8.2 g of pyridine as imidiation catalysts were added thereto, followed by reaction at 40° C. for 3 hours to prepare a soluble polyimide resin solution. This solution was poured into 0.6 L of methanol, and the obtained precipitates were collected by filtration and dried to obtain a white soluble polyimide (SPI) resin. The molecular weights of the obtained soluble polyimide were measured in the same manner as in Preparation Example 1 and as a result, the number average molecular weight was 13,430 and the weight average molecular weight was 26,952. 1 g of this powder was dissolved in 15 g of γ-BL and 4 g of BCS to prepare a soluble polyimide solution having a soluble polyimide concentration of 5 mass % and a BCS concentration of 20 mass % to obtain a liquid crystal aligning agent.

Preparation Example 38

TDA/p-PDA, DAOOB (10) (SPI):CBDA, PMDA (50)/4-ABA=2:8

20 Mass % of the liquid crystal aligning agent prepared in Preparation Example 37 and 80 mass % of the liquid crystal aligning agent prepared in Preparation Example 21 were blended to obtain a liquid crystal aligning agent.

Comparative Preparation Example 1

CBDA/p-PDA 18.24 g (0.093 mol) of CBDA and 10.81 g (0.1 mol) of p-PDA were reacted in 334 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 72,383 and a weight average molecular weight of 180,395 was obtained. Further, to this solution, poor solvents BCS and NMP were added so that the polyamic acid concentration would be 5 mass % and the BCS concentration would be 20 mass % to prepare a liquid crystal aligning agent.

Comparative Preparation Example 2

CBDA/BAPB 18.63 g (0.095 mol) of CBDA and 29.23 g (0.1 mol) of BAPB were reacted in 271 g of NMP at room temperature for 10 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 25,126 and a weight average molecular weight of 50,853 was obtained. Further, to this solution, poor solvents BCS and NMP were added so that the polyamic acid concentration would be 5 mass % and the BCS concentration would be 20 mass % to prepare a liquid crystal aligning agent.

Comparative Preparation Example 3

CBDA, PMDA (80)/DDM 3.92 g (0.02 mol) of CBDA, 16.14 g (0.074 mol) of PMDA and 19.83 g (0.1 mol) of DDM were reacted in 226 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 25,316 and a weight average molecular weight of 54,214 was obtained. Further, to this solution, poor solvents BCS and NMP were added so that the polyamic acid concentration would be 5 mass % and the BCS concentration would be 20 mass % to prepare a liquid crystal aligning agent.

Comparative Preparation Example 4

CBDA/6-DAN 1.49 g (0.095 mol) of CBDA and 1.27 g (0.1 mol) of 6-DAN were reacted in 31.7 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 18,669 and a weight average molecular weight of 35,820 was obtained. Further, to this solution, poor solvents BCS and NMP were added so that the polyamic acid concentration would be 5 mass % and the BCS concentration would be 20 mass % to prepare a liquid crystal aligning agent.

Comparative Preparation Example 5

CBDA/DDM 19.02 g (0.097 mol) of CBDA and 19.83 g (0.1 mol) of DDM were reacted in 349 g of NMP at room temperature for 5 hours to prepare a polyamic acid solution. The polymerization reaction proceeded easily and uniformly, and the molecular weights were measured in the same manner as in Preparation Example 1 and as a result, a solution of a polyamic acid having a number average molecular weight of 42,439 and a weight average molecular weight of 80,710 was obtained. Further, to this solution, poor solvents BCS and NMP were added so that the polyamic acid concentration would be 5 mass % and the BCS concentration would be 20 mass % to prepare a liquid crystal aligning agent.

Comparative Preparation Example 6

PMDA/BAPE 19.87 g (0.091 mol) of PMDA and 21.21 g (0.1 mol) of BAPE were reacted in 233 g of NMP at room temperature to prepare a polyamic acid solution. The polymerization reaction proceeded easily and uniformly, but 5 hours later, the solution was clouded.

Comparative Preparation Example 7

CBDA/p-PDA, DAE (50)

18.83 g (0.096 mol) of CBDA, 5.41 g (0.05 mol) of p-PDA and 3.0 g (0.05 mol) of DAE were reacted in 245 g of NMP at room temperature to prepare a polyamic acid solution. However, during the polymerization reaction, white precipitates formed, and the polymerization did not proceed uniformly. The precipitates did not disappear even after stirring for 24 hours.

Comparative Preparation Example 8

CBDA, TDA (20)/p-PDA, DADOB (20)

14.71 g (0.075 mol) of CBDA, 6.01 g (0.02 mol) of TDA, 9.73 g (0.09 mol) of p-PDA and 2.92 g (0.01 mol) of DADOB were reacted in 189 g of NMP at room temperature for 5 hours to prepare a polyamic acid solution. 50 g of the polyamic acid solution was diluted to 5 mass % with NMP, and 22.3 g of acetic anhydride and 10.4 g of pyridine as imidation catalysts were added, followed by reaction at 40° C., but the polyamic acid became unsoluble during the reaction.

Example 1

Using the liquid crystal aligning agent obtained in Preparation Example 1, the voltage holding characteristics, the charge accumulation characteristics and the storage stability were evaluated. The results are shown in Table 1.
<Evaluation of Voltage Holding Characteristics>

(Voltage Holding Ratio)
The liquid crystal aligning agent was spin-coated on a glass substrate provided with ITO electrodes, dried for 5 minutes on a hot plate of 80° C. and then baked for 30 minutes in a hot air circulation oven at 220° C. to form a coated film having a thickness of 100 nm. This coated surface was subjected to rubbing by means of a rayon cloth by a rubbing apparatus having a roll diameter of 120 mm under conditions of a roll rotational speed of 700 rpm, a roll advancing speed of 10 mm/sec. and a pushing amount of 0.6 mm, to obtain a substrate provided with a liquid crystal alignment film.

Two sheets of the above substrate provided with a liquid crystal alignment film were prepared, a spacer of 6 μm was sprayed on a liquid crystal alignment film of one sheet, then a sealing agent was printed thereon, and the other substrate was bonded so that the liquid crystal alignment film surfaces faced each other and that the rubbing directions crossed each other, whereupon the sealing agent was cured to prepare a void cell. To this void cell, liquid crystal MLC-2003 (manufactured by Merck Japan Limited) was injected by a reduced pressure injection method, and the injection inlet was sealed to obtain a twist nematic liquid crystal cell. The cell was observed by a polarizing microscope and as a result, the liquid crystals were uniformly aligned.

To the twist nematic liquid crystal cell, a voltage of 4 V was applied for 60 μs at a temperature of 23° C., and the voltage after 16.67 ms was measured, whereby to what extent the voltage was maintained, was calculated as a voltage holding ratio (measurement was carried out by means of a voltage holding ratio measuring apparatus VHR-1 manufactured by TOYO Corporation, under conditions of voltage: ±4 V, pulse width: 60 μs and flame period: 16.67 ms). Further, a similar measurement was carried out also at a temperature of 60° C.
<Evaluation of Charge Accumulation Characteristics>

(Residual Voltage after Application of DC Voltage)
Rectangular waves of ±3 V/30 Hz having a DC voltage of 3 V superimposed were applied to the twist nematic liquid crystal cell of which the voltage holding characteristics were measured, for 60 minutes at a temperature of 23° C., and the residual voltage remaining in the liquid crystal cell immediately after switching off the DC 3 V was measured by an optical flicker elimination method.
<Storage Stability Evaluation>

The liquid crystal aligning agent was stored at 23° C. or −20° C., and presence or absence of precipitations after three months was confirmed.

Examples 2 to 37

Using each of the liquid crystal aligning agents of the present invention obtained in Preparation Examples 2 to 38, a liquid crystal cell was prepared in the same manner as in Example 1. The cell was observed by a polarizing microscope and as a result, liquid crystals were uniformly aligned. Using the liquid crystal cell, the voltage holding ratio, the charge accumulation characteristics and the storage stability were evaluated in the same manner as in Example 1. The results are shown in Table 1 mentioned hereinafter.

Comparative Examples 1 to 5

Using each of the liquid crystal aligning agents obtained in Comparative Preparation Examples 1 to 5, evaluation was carried out in the same manner as in Example 1. The results are shown in Table 1 mentioned hereinafter.

In Comparative Example 1, precipitations were confirmed in the liquid crystal aligning agent after three months. In Comparative Example 2, the voltage holding ratio was low. In the liquid crystal aligning agents obtained in Comparative Preparation Examples 3 and 4, precipitations were confirmed after one month. In Comparative Example 5, the charge accumulation characteristics were poor.

TABLE 1

| | Liquid crystal aligning agent | Resin component | Voltage holding ratio (%) 23° C. | Voltage holding ratio (%) 60° C. | Accumulated charge (V) | Storage stability 23° C. | Storage stability −20° C. |
|---|---|---|---|---|---|---|---|
| Ex. 1 | Prep. Ex. 1 | CBDA/4-ABA | 99.2 | 97.4 | 0.5 | No precipitation | No precipitation |
| Ex. 2 | Prep. Ex. 2 | CBDA/3-ABA | 99.3 | 97.6 | 0.5 | No precipitation | No precipitation |
| Ex. 3 | Prep. Ex. 3 | CBDA/4-APhA | 99.0 | 95.7 | 0.7 | No precipitation | No precipitation |
| Ex. 4 | Prep. Ex. 4 | CBDA/6-ANaMA | 99.0 | 96.0 | 0.2 | No precipitation | No precipitation |
| Ex. 5 | Prep. Ex. 5 | CBDA/6-ANaEA | 99.0 | 95.8 | 0.2 | No precipitation | No precipitation |
| Ex. 6 | Prep. Ex. 6 | TDA/6-ANaMA | 99.0 | 96.0 | 0.2 | No precipitation | No precipitation |
| Ex. 7 | Prep. Ex. 7 | TDA/6-ANaEA | 99.0 | 95.8 | 0.2 | No precipitation | No precipitation |
| Ex. 8 | Prep. Ex. 8 | CBDA/p-PDA, 4-ABA (50) | 99.0 | 96.2 | 0.2 | No precipitation | No precipitation |
| Ex. 9 | Prep. Ex. 9 | CBDA/p-PDA, 6-ANaMA (50) | 99.3 | 96.5 | 0.2 | No precipitation | No precipitation |
| Ex. 10 | Prep. Ex. 10 | CBDA/p-PDA, 6-ANaEA (50) | 99.3 | 96.0 | 0.2 | No precipitation | No precipitation |
| Ex. 11 | Prep. Ex. 11 | CBDA/4-ABA, DADOB (20) | 99.3 | 97.8 | 0.6 | No precipitation | No precipitation |
| Ex. 12 | Prep. Ex. 12 | CBDA/p-PDA, 3-ABA (10) | 99.0 | 97.5 | 0.2 | No precipitation | No precipitation |
| Ex. 13 | Prep. Ex. 13 | TDA/4-ABA (SPI) | 99.4 | 98.1 | 0.3 | No precipitation | No precipitation |
| Ex. 14 | Prep. Ex. 14 | TDA/4-APhA (SPI) | 99.0 | 96.5 | 0.9 | No precipitation | No precipitation |
| Ex. 15 | Prep. Ex. 15 | CBDA, TDA (20)/3-ABA, DADOB (10) (SPI) | 99.3 | 97.5 | 0.5 | No precipitation | No precipitation |
| Ex. 16 | Prep. Ex. 16 | PMDA/4-ABA | 99.0 | 96.0 | 0 | No precipitation | No precipitation |
| Ex. 17 | Prep. Ex. 17 | PMDA/3-ABA | 99.0 | 96.0 | 0 | No precipitation | No precipitation |
| Ex. 18 | Prep. Ex. 18 | PMDA/4-APhA | 98.9 | 95.0 | 0 | No precipitation | No precipitation |
| Ex. 19 | Prep. Ex. 19 | PMDA/6-ANaMA | 99.1 | 95.5 | 0 | No precipitation | No precipitation |
| Ex. 20 | Prep. Ex. 20 | PMDA/6-ANaEA | 99.1 | 95.0 | 0 | No precipitation | No precipitation |
| Ex. 21 | Prep. Ex. 21 | CBDA, PMDA (50)/4-ABA | 99.2 | 97.1 | 0 | No precipitation | No precipitation |
| Ex. 22 | Prep. Ex. 22 | CBDA, PMDA (80)/4-ABA | 99.0 | 96.6 | 0 | No precipitation | No precipitation |
| Ex. 23 | Prep. Ex. 23 | CBDA, PMDA (80)/3-ABA | 99.1 | 96.7 | 0 | No precipitation | No precipitation |
| Ex. 24 | Prep. Ex. 24 | CBDA, PMDA (80)/4-APhA | 98.9 | 95.5 | 0 | No precipitation | No precipitation |
| Ex. 25 | Prep. Ex. 25 | CBDA, PMDA (80)/6-ANaMA | 98.9 | 96.0 | 0 | No precipitation | No precipitation |
| Ex. 26 | Prep. Ex. 26 | CBDA, PMDA (80)/6-ANaEA | 99.2 | 95.5 | 0 | No precipitation | No precipitation |
| Ex. 27 | Prep. Ex. 27 | CBDA, PMDA (80)/DDM, 4-ABA (50) | 99.2 | 97.1 | 0 | No precipitation | No precipitation |
| Ex. 28 | Prep. Ex. 28 | CBDA, PMDA (80)/DDM, 4-ABA (10) | 99.2 | 97.1 | 0 | No precipitation | No precipitation |
| Ex. 29 | Prep. Ex. 29 | CBDA, PMDA (80)/DDM, 6-ANaMA (10) | 99.2 | 96.9 | 0 | No precipitation | No precipitation |
| Ex. 30 | Prep. Ex. 30 | CBDA, PMDA (80)/DDM, 6-ANaEA (10) | 99.2 | 96.5 | 0 | No precipitation | No precipitation |
| Ex. 31 | Prep. Ex. 31 | CBDA, PMDA (80)/BAPB, 4-ABA (70) | 99.0 | 96.1 | 0 | No precipitation | No precipitation |
| Ex. 32 | Prep. Ex. 32 | PMDA/4-ABA, DAHOB (10) | 99.0 | 97.5 | 0 | No precipitation | No precipitation |
| Ex. 33 | Prep. Ex. 33 | CBDA, PMDA (80)/4-ABA, DADPA (30), BAPP (10) | 99.1 | 97.1 | 0 | No precipitation | No precipitation |
| Ex. 34 | Prep. Ex. 34 | CBDA, PMDA (80)/4-ABA, p-PDA (50) | 99.0 | 96.3 | 0 | No precipitation | No precipitation |
| Ex. 35 | Prep. Ex. 35 | CBDA, PMDA (80)/4-ABA, BAPP (10) | 99.1 | 97.0 | 0 | No precipitation | No precipitation |
| Ex. 36 | Prep. Ex. 36 | CBDA/4-ABA:PMDA/ 4-ABA = 2:8 | 99.1 | 97.1 | 0 | No precipitation | No precipitation |

TABLE 1-continued

| Liquid crystal aligning agent | Resin component | Voltage holding ratio (%) 23° C. | 60° C. | Accumulated charge (V) | Storage stability 23° C. | −20° C. |
|---|---|---|---|---|---|---|
| Ex. 37 | Prep. Ex. 38 | TDA/p-PDA, DAOOB (10) (SPI):CBDA, PMDA (50)/ 4-ABA = 2:8 | 99.4 | 98.1 | 0 | No precipitation | No precipitation |
| Comp. Ex. 1 | Comp. Prep. Ex. 1 | CBDA/p-PDA | 99.2 | 97.0 | 0.2 | Precipitation observed | Precipitation observed |
| Comp. Ex. 2 | Comp. Prep. Ex. 2 | CBDA/BAPB | 95.0 | 90.4 | 1.5 | No precipitation | No precipitation |
| Comp. Ex. 3 | Comp. Prep. Ex. 3 | CBDA, PMDA (80)/DOM | 99.2 | 97.0 | 0 | Precipitation observed | Precipitation observed |
| Comp. Ex. 4 | Comp. Prep. Ex. 4 | CBDA/6-DAN | 99.1 | 94.1 | 0.2 | Precipitation observed | Precipitation observed |
| Comp. Ex. 5 | Comp. Prep. Ex. 5 | CBDA/DDM | 99.3 | 97.2 | 0.9 | No precipitation | No precipitation |

Example 38

Using the liquid crystal aligning agent of the present invention obtained in Preparation Example 1, a UV absorption spectrum of the liquid crystal alignment film was measured. The results are shown in FIG. 1.

<UV Absorption Spectrum Measurement>

The liquid crystal aligning agent was spin-coated on a quartz substrate, dried for 5 minutes on a hot plate of 80° C. and then baked for 30 minutes in a hot air circulation oven at 230° C. to form a coated film having a thickness of 100 nm. The UV absorption spectrum of this substrate provided with a liquid crystal alignment film was measured by using UV-3100PC(SHIMAZU).

Examples 39 and 40

Using the liquid crystal aligning agents of the present invention obtained in Preparation Examples 2 and 3, evaluation was carried out in the same manner as in Example 38. The results are shown in FIG. 1.

Comparative Example 6

Using the liquid crystal aligning agent of the present invention obtained in Comparative Preparation Example 5, evaluation was carried out in the same manner as in Example 38. As a result, the absorbance at from 250 nm to 400 nm was high as compared with Examples 38 to 40.

Further, the UV absorption spectrum is shown in FIG. 1.

INDUSTRIAL APPLICABILITY

The liquid crystal aligning agent of the present invention is excellent in the productivity and the storage stability, and is capable of providing a liquid crystal alignment film excellent in the electrical characteristics. Accordingly, the liquid crystal display device prepared by using the liquid crystal aligning agent of the present invention can be made to be a liquid crystal display device which is less susceptible to lowering of contrast or to image assistance, and it is useful for display devices of various systems employing nematic liquid crystal, such as a TN liquid crystal display device, an STN liquid crystal display device, a TFT liquid crystal display device, an OCB liquid crystal display device and further an in-plane switching liquid crystal display device and a vertically aligned liquid crystal display device. Further, by selecting the liquid crystal to be used, it can be used also for ferroelectric and antiferroelectric liquid crystal display devices. Further, a conventional liquid crystal alignment film has a high absorbance in the visible to UV region and is thereby decomposed when irradiated with light for a long time, and its liquid crystal display characteristics deteriorate in some cases, whereas the liquid crystal aligning agent of the present invention has a low absorbance in the visible to UV region and is thereby suitably used for a large-size television with intense back light, a liquid crystal display device for a liquid crystal projector, etc.

The entire disclosures of Japanese Patent Application No. 2004-132611 filed on Apr. 28, 2004 and Japanese Patent Application No. 2005-068290 filed on Mar. 11, 2005 including specifications, claims, drawings and summaries are incorporated herein by reference in their entireties.

The invention claimed is:

1. A liquid crystal display device employing a liquid crystal alignment film obtained by employing a liquid crystal alignment agent comprising at least one member selected from the group consisting of a polyamic acid obtained by polymerization of a diamine component with a tetracarboxylic dianhydride component, and a polyimide obtained by cyclodehydration of the polyamic acid, wherein the diamine component contains at least one of diamines represented by the following formula [1]:

$$H_2N\text{-}A\text{-}R\text{—}NH_2 \qquad [1]$$

wherein A is a bivalent organic group comprising a benzene ring or an aromatic condensed ring, provided that one or more optional hydrogen atoms in the benzene ring or the aromatic condensed ring may be substituted by a monovalent organic group other than an amino group, and R is a $C_{1-10}$ bivalent saturated hydrocarbon group.

2. The liquid crystal display device according to claim 1, wherein A in the formula [1] is a bivalent aromatic group selected from the formulae [2-1] to [2-4]:

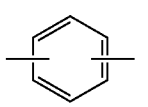

[2-1]

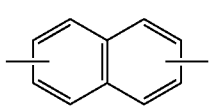

[2-2]

-continued

[2-3]
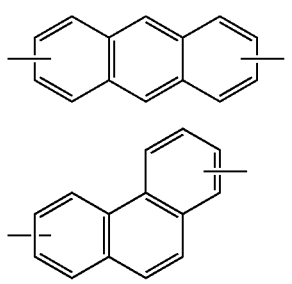

[2-4]

provided that one or more optional hydrogen atoms in the benzene ring or the aromatic condensed ring may be substituted by a monovalent organic group other than an amino group.

3. The liquid crystal display device according to claim 1, wherein R in the formula [1] is represented by the following formula [3]:

$$—(CH_2)_{n1}\text{-}(Q)_{n2}\text{-}(CH_2)_{n3}— \quad [3]$$

wherein Q is a $C_{3-7}$ hydrocarbon ring, each of n1 and n3 is an integer of from 0 to 7, and n2 is an integer of 0 or 1, provided that n1, n2 and n3 are not simultaneously 0.

4. The liquid crystal display device according to claim 3, wherein Q is cyclobutane, cyclopentane or cyclohexane.

5. The liquid crystal display device according to claim 1, wherein R is $—(CH_2)_{n1}—$, $—(CH_2)_{n1}\text{-}(Q)_{n2}$ or $\text{-}(Q)_{n2}—(CH_2)_{n3}—$, wherein Q is a $C_{3-7}$ hydrocarbon ring, each of n1 and n3 is an integer of from 1 to 7, and n2 is an integer of 1.

6. The liquid crystal display device according to claim 5, wherein Q is cyclobutane, cyclopentane or cyclohexane.

7. The liquid crystal display device according to claim 1, wherein the diamine component contains a diamine represented by the formula [4]:

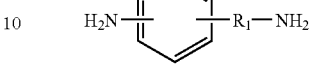

[4]

wherein $R_1$ is a $C_{1-10}$ bivalent saturated hydrocarbon group, provided that one or more optional hydrogen atoms in the benzene ring may be substituted by a monovalent organic group other than an amino group.

8. The liquid crystal display device according to claim 1, wherein the diamine component contains at least one of diamines represented by the formula [5]:

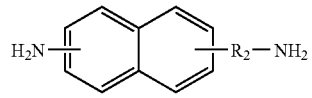

[5]

wherein $R_2$ is a $C_{1-10}$ bivalent saturated hydrocarbon group, provided that one or more optional hydrogen atoms in the naphthalene ring may be substituted by a monovalent organic group other than an amino group.

* * * * *